United States Patent [19]

Skibo

[11] Patent Number: 5,015,742

[45] Date of Patent: May 14, 1991

[54] SYNTHESIS AND ELUCIDATION OF AZAMITOSENE AND IMINOAZAMITOSENE

[75] Inventor: Edward B. Skibo, Scottsdale, Ariz.

[73] Assignee: Arizona Board of Regents, Tempe, Ariz.

[21] Appl. No.: 486,977

[22] Filed: Feb. 28, 1990

[51] Int. Cl.$^5$ ............... C07D 235/30; C07D 235/04; C07D 487/00

[52] U.S. Cl. .................................. 548/323; 548/325; 548/327

[58] Field of Search ................. 548/325, 323, 327

Primary Examiner—Mary C. Lee
Assistant Examiner—Joseph K. McKane
Attorney, Agent, or Firm—Richard R. Mybeck

[57] ABSTRACT

The synthesis of 2,3-dihydro-1H-pyrrolo[1,2-a]benzimidazole-5,8-diones (azamitosenes was carried out in conjunction with the design of potential DNA crosslinkers activated by reduction (reductive alkylation). These quinones resemble mitosene antitumor agents, but are based on the benzimidazole nucleus rather than the indole nucleus. Preliminary results indicate the azamitosenes are potent antitumor agents. Iminoquinone derivatives of azamitosenes (iminoazamitosenes) were synthesized as reductive alkylating agents exhibiting low oxygen toxicity. The iminoazamitosenes are hydrolytically stable in neutral buffers and undergo buffer catalyzed syn/anti isomerization at the imino center. Electrochemical and oxygen reactivity studies in aqueous buffers indicate the change from quinone to iminoquinone is accompanied by an increase in reduction potential and a decrease in oxygen reactivity of the corresponding reduced species.

24 Claims, 1 Drawing Sheet

SYNTHESIS AND ELUCIDATION OF AZAMITOSENE AND IMINOAZAMITOSENE

INTRODUCTION

The present invention relates to the synthesis and elucidation of new compounds and more particularly to the synthesis and elucidation of azamitosenes and iminoazamitosenes.

BACKGROUND OF THE INVENTION

Mitomycins and the corresponding mitosene analogues are well-known examples of reductive alkylating quinones. The reductive alkylation process involves the formation of an alkylating quinone methide species upon reduction of the quinone and elimination of a leaving group. Since tumor cells possess a low reduction potential environment, there is a great deal of interest in reductive alkylating quinones as selective antitumor agents. Thus, a wide range of mitomycin and mitosene derivatives have been prepared in an effort to optimize antitumor activity. All of these derivatives possess the indole ring nucleus, but with a variety of substituents.

Our efforts revealed that benzimidazole-based reductive alkylating agents are also capable of forming an alkylating quinone methide species (See: Skibo, E. B., *J. Org. Chem*, 1986, 51, 522). Altering the indole nucleus of mitosene to benzimidazole (azamitosene) therefore became important in terms of antitumor agent development.

A problem with reductive alkylating agents arises from the formation of toxic oxygen species when cycling between the quinone and hydroquinone forms of the agent. (See: Doroshow, J. H., *Cancer Res.*, 1983, 43, 460; and Begleiter, A., *Cancer Res.*, 1983, 43, 481). In the case of daunomycin, the iminoquinone derivative of this reductive alkylating agent possesses lower oxygen toxicity than the quinone derivative. (See: Tong et al, *J. Med. Chem.*, 1979, 22, 36). Thus, our efforts also included the preparation of hydrolytically stable iminoazamitosenes and detailed studies of their electrochemistry and oxygen reactivity.

BRIEF SUMMARY OF THE DISCLOSURE

The present invention relates to the synthesis of those azamitosenes and the iminoazomitosenes shown below. The azamitosenes possess alkylating centers at the 3- and 6- positions which permits DNA crosslinking activity. The iminoazamitosenes are hydrolytically stable below pH 6 and studies shown that the conversion of quinone to iminoquinone is accompanied by an increase in reduction potential as well as a decrease in the oxygen reactivity of the reduced (aminophenol) form.

The azamitosenes have the structural formula

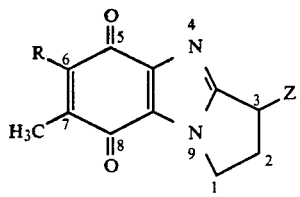

wherein:

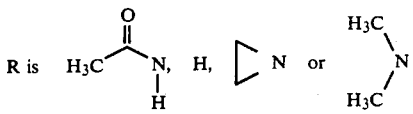

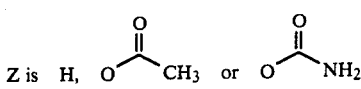

The iminoazamitosenes hereof have the structural formula:

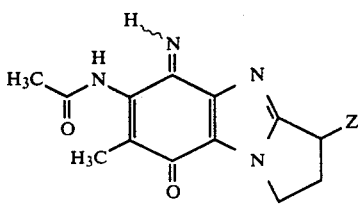

wherein:

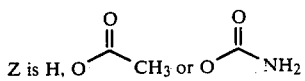

DESCRIPTION OF PREFERRED EMBODIMENTS

Figure 1:
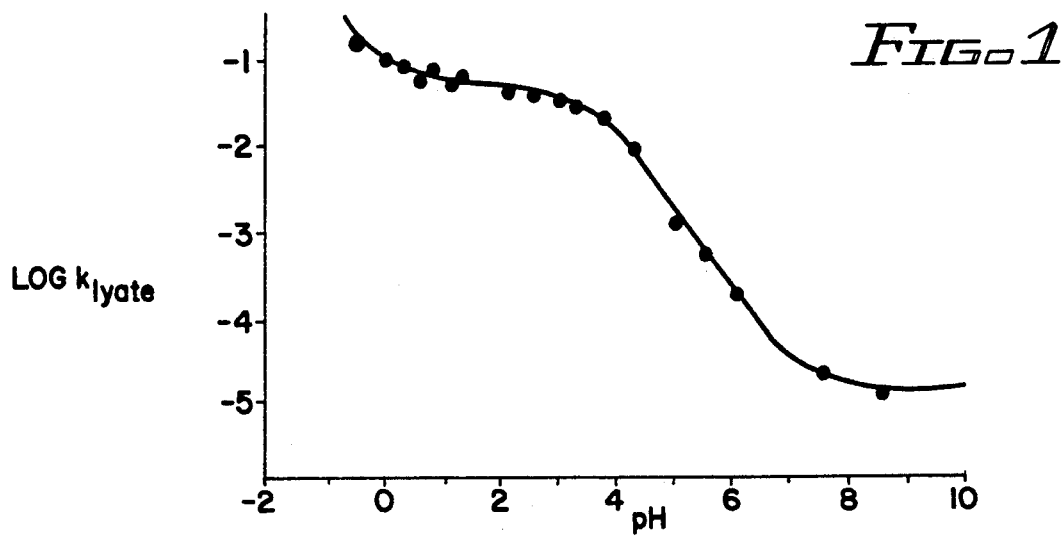
FIG. 1 shows a plot of $k_{lyate}$ vs pH for the first-order reactions of syn 2a in aerobic buffer.

The present invention relates to the synthesis and elucidarion of the azamitosenes and iminoazamitosenes shown above and the details thereof shall now be described.

Azamitosene and Iminoazamitosene Synthesis

Preparation of the azamitosene ring system (2,3-dihydro-1H-pyrrolo[1,2-a]benzimidazole) was completed by using the Lewis acid catalyzed cyclization of an ortho-nitropyrrolidinobenzene derivative (e.g., compound 3—>4 in Scheme 1 and compound 10—>12 in Scheme 2) and by the oxidative cyclization of a diacetamido pyrrolidinobenzene derivative (e.g., 11—>13). (See: Grantham et al, J. Chem. Soc. (C). 1969, 70 Nair et al, *J. Am. Chem. Soc.*, 1961, 83, 3518). The first reaction was employed to prepare azamitosenes having a leaving group at the 3- position and the second reaction was employed to prepare the 3-unsubstituted derivatives. Quinone and iminoquinone elaboration was carried out by Fremy oxidation of aromatic amine derivatives in pH~3 and in pH=7.0 aqueous buffers, respectively.

The synthesis of the antitumor agents 1c,d is shown in Scheme 1. The pyrrolo[1,2-a]benzimidazole derivative 4 was brominated at the 6-position so as to direct nitration to the 5-position in the next step (5—>6). Catalytic reduction of 6 resulted in both amine reduction and hydrogenolysis of the bromo substituent to afford 7c. The acetate leaving group of 6 was converted to carbamate (6—>8) followed by catalytic reduction to afford 7d. Finally, Fremy oxidation of 7c,d to 9c,d and then reductive addition of ethyleneimine in the presence of air afforded 1c,d.

The synthesis of the stabilized iminoquinones syn-2a,b and anti-2a,b is shown in Scheme 2. Fremy oxidation of 16a,b in pH 7.0 phosphate buffer afforded a syn/anti mixture of iminoquinone isomers, which can be separated by fractional crystallization as described hereinafter in greater detail.

Structural assignments of the isomers were possible using $^1$H NMR chemical shifts obtained in dimethyl sulfoxide-$d_6$ (DMSO $d_6$) The syn/anti isomers also possess different IR and UV-visible spectra. The latter permitted kinetic studies of the syn/anti isomerization process in aqueous buffer (vide infra). Intramolecular proton transfer only in the syn isomer is likely responsible for all of the observed spectral differences.

The $^1$H NMR chemical shifts (dimethyl sulfoxide-$d_6$) of the acetamido methyl and 7-methyl groups of syn 2a are shifted upfield relative to those of anti 2a. This observation is consistent with the formation of a delocalized negative charge at the centers bearing the methyl groups in the syn isomer upon intramolecular proton transfer. In contrast, the imino-nitrogen lone pair of anti 2a is anti to the amide proton and a zwitterion cannot form. Nuclear Overhauser effects (NOE) are also consistent with the assigned structures in Scheme 3. In the zwitterionic form, the iminium proton at $\delta 9.19$ shows NOE interactions with both the acetamido and 7 methyls while the $\delta 6.24$ iminium proton does not. On the other hand, both nitrogen-substituted protons of anti 2a show NOE interaction with these methyls. The NOE interactions for the $\delta 9.59$ proton with the methyl groups are much greater than those observed for the $\delta 11.42$ proton, which led to the assignments shown in Scheme 3 below. These assignments are consistent with literature values of imino protons chemical shifts ($\delta = 11.2$) and with the acetamido nitrogen proton chemical shifts ($\delta 7.5$–9.3) reported herein.

The IR spectra (KBr pellet) of syn and anti 2a also supports intramolecular proton transfer in the former compound. The quinone carbonyl stretching frequency of anti 2a (1683 cm$^{-1}$) is greater than that of syn 2a (1652 cm$^{-1}$) due to the decrease in carbonyl bond order in the zwitterion.

Iminoquinone Fate in Aqueous Buffers. The fate of syn and anti 2a, $6.8 \times 10^{-5}$ M in aerobic aqueous buffer ($\mu = 1.0$, KCl), was studied at 30° C. over the pH range of 0 to 9. Outlined in Scheme 4 below, are the pertinent equilibria and hydrolytic reactions of 2a in aqueous buffer. Above pH 7, the predominate reaction is equilibrium formation of a syn/anti mixture of 2a by general acid/base catalyzed processes. Much below pH 7, the predominate reaction is acid-catalyzed hydrolysis of 2a to the corresponding quinone 1a.

The studies which led to the mechanism outlined in Scheme 4 will now be described. Both hydrolysis and the equilibrium isomerization of pure syn 2a or pure anti 2a are associated with an absorbance change at 320 nm. Plots of absorbance vs time obeyed a first-order rate law over the entire pH range studied. The $k_{obsd}$ values were dependent on the concentration of the buffers employed to hold pH over the range of pH=3 to 9. Lyate-dependent values of $k_{obsd}$ ($k_{lyate}$) were obtained by measuring $k_{obsd}$ values over a 10-fold range of buffer concentration at constant pH and then extrapolating to the $k_{lyate}$ value at zero buffer concentration. A plot of the log ($k_{lyate}$) values vs pH is shown in FIG. 1.

Preparative hydrolysis of syn 2a at pH 4 resulted in the isolation of 1a in 90% yield. The UV-visible spectra of completed reactions from pH 0 to pH 6 indicated quantitative formation of 1a. Below pH 7, the preparative reaction of pure syn 2a afforded a mixture of isomers; [syn 2a]/[anti 2a]=0.7 by $^1$H NMR.

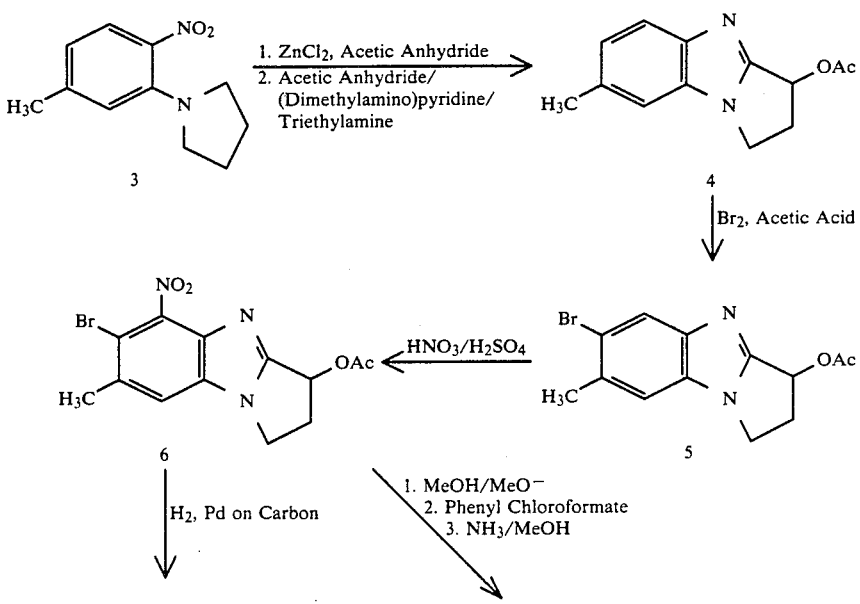

SCHEME 1

-continued
SCHEME 1
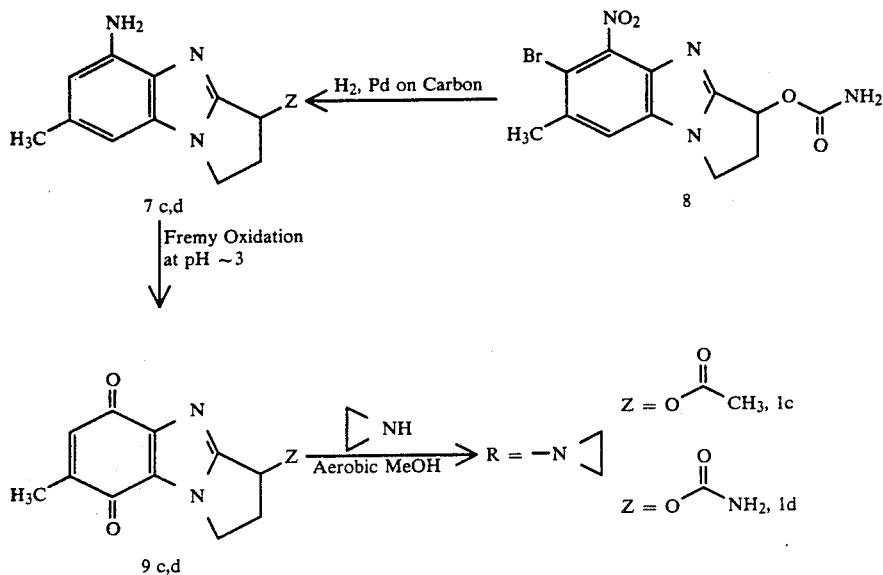
SCHEME 2
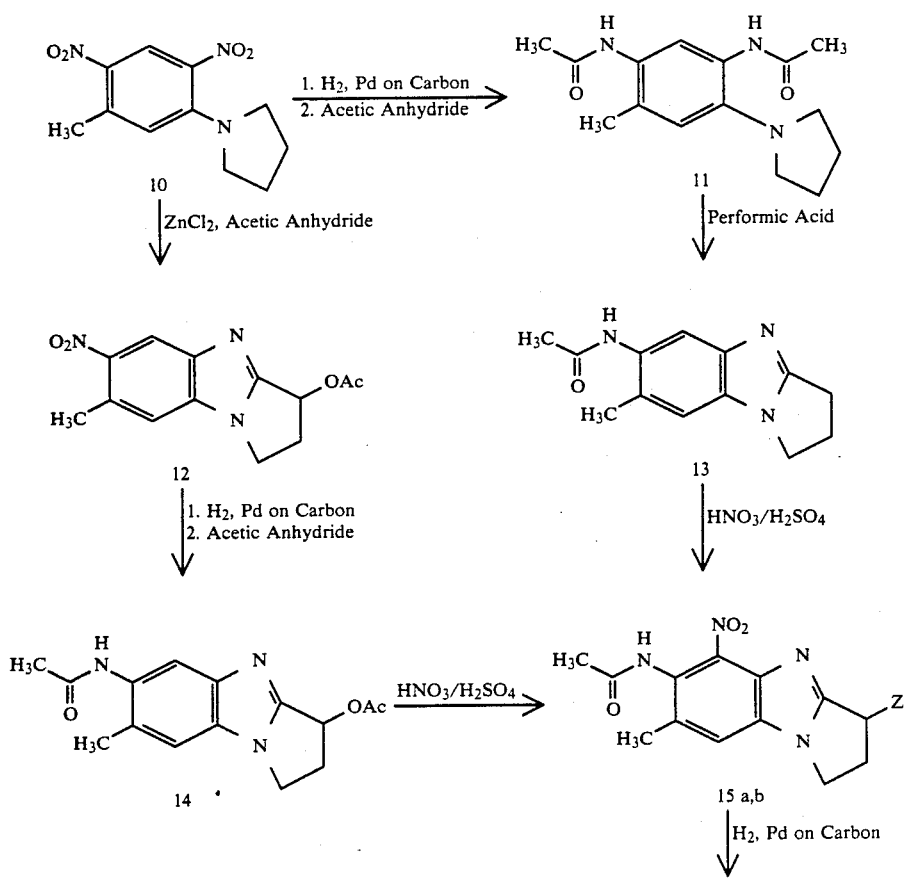

-continued
SCHEME 2

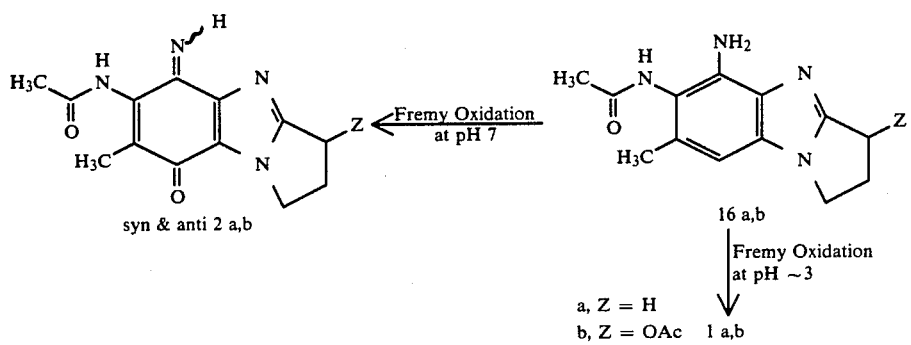

a, Z = H
b, Z = OAc  1 a,b

SCHEME 3

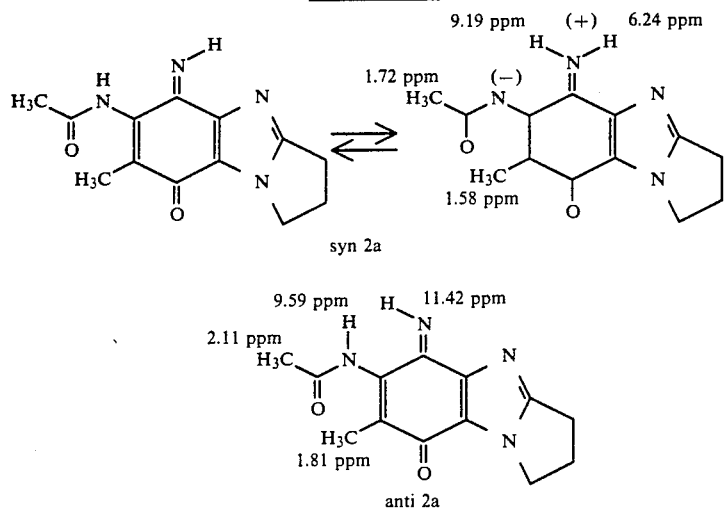

$$\frac{a_H k_3}{K_{a5}} + \frac{a_H k_2}{a_H + K_{a4}} + (k_1 + k_{-1}) = k_{lyate} \quad \text{Equation 1}$$

The pH profile of FIG. 1 indicates quinone formation occurs from the monoprotonated and diprotonated forms of 2a. Thus the plateau (slope −1 to 0) in the acid region corresponds to the acid dissociation $2aH^+ \rightleftharpoons 2a + H^+$ ($pK_a \sim 2.5$) and rate-determining hydrolysis of the protonated species. At very high acidity, the rates of hydrolysis again increase with a slope of −1 on the profile, which is attributed to the acid dissociation $2aH^{2+} \rightleftharpoons 2aH^+ + H^+$ ($pK_a < 0$) and rate-determining hydrolysis of the diprotonated species. The small $pK_a$ value of the diprotonated species and the large rates of hydrolysis did not permit the second plateau to be reached, however. Electrochemical studies (vide infra) provided evidence of a diprotonated imine species in strong acid. The pH profile of FIG. 1 also indicates the syn/anti equilibration process is either water-catalyzed or spontaneous above pH 7 (i.e., the slope of the profile is zero).

The rate law for the reaction of pure syn 2a, based on the mechanism shown in Scheme 4 below, is provided in Equation 1:

wherein: $k_1$, $k_{-1}$, $k_2$, $k_3$, $K_{a4}$ and $K_{a5}$ are constants found in Scheme 4 and $a_H$ is the proton activity determined with a pH electrode. The first term of equation 1 pertains to the hydrolysis of $2aH^{2+}$ under the conditions $a_H < K_{a5}$, the second term pertains to hydrolysis of 2aH and third term pertains to the syn/anti equilibration. The solid line shown in FIG. 1 was computer generated with equation 1 using $k_3/K_{a5} = 4.5 \times 10^{-2}$ $M^{-1}s^{-1}$, $k_2 = 4.8 \times 10^{-2} s^{-1}$, $pK_{a4} = 3.4$, and $k_1 + k_{-1} = 1.03 \times 10^{-5} s^{-1}$. Consistent with the postulated mechanism, the kinetically-obtained value of $pK_{a4}$ approximates the value obtained by spectrophotometric titration (2.6±0.3).

The hydrolysis of 2a is also subject to general acid catalysis over the range pH 3.5 to 6; $k_{ga}$ for acetic acid was found to be $3 \times 10^{-3} M^{-1}s^{-1}$. Since 2a is largely protonated at the low end of this pH range, general acid catalysis must not pertain to rate-determining protonation of the imine nitrogen. An alternative mechanism is general-base catalyzed addition of water to the protonated imine as shown below, structure 17.

SCHEME 4

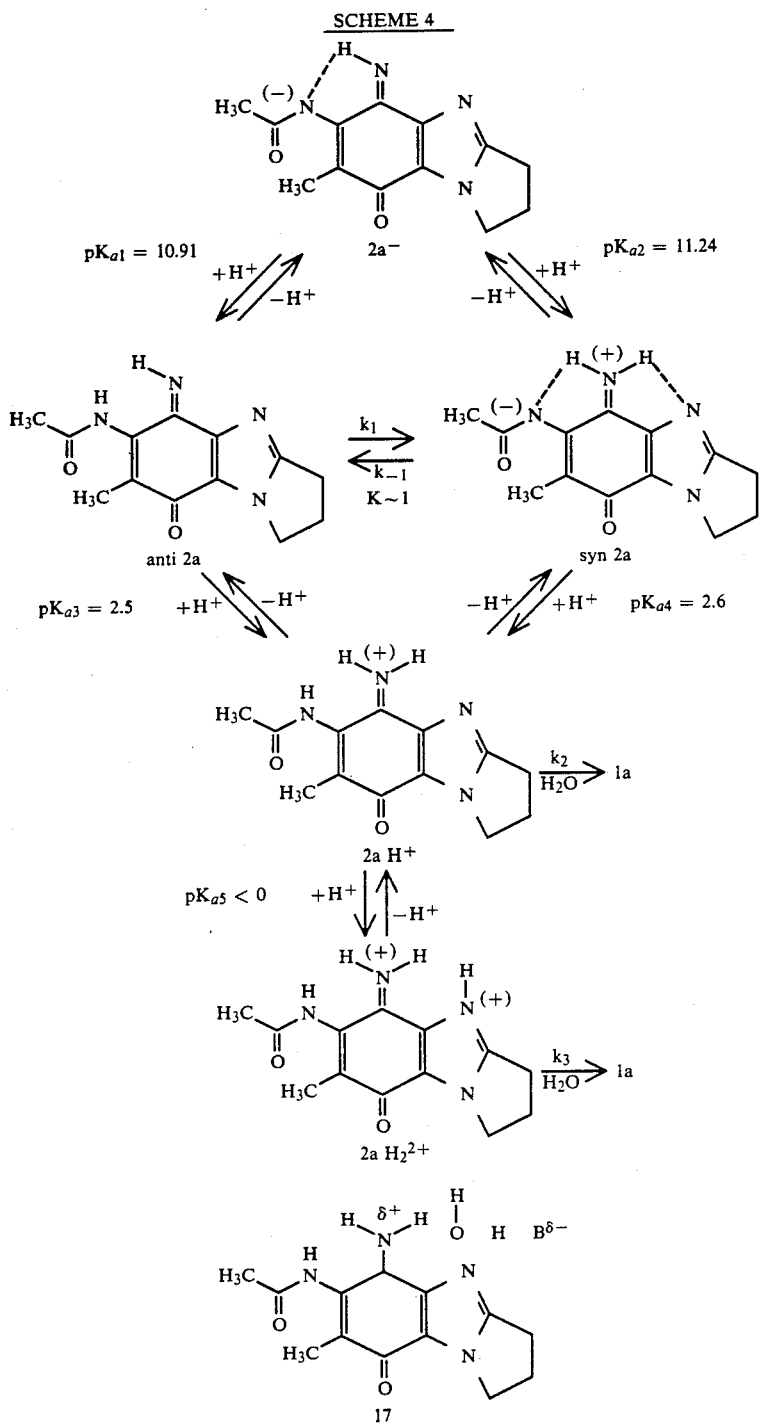

This mechanism is a specific acid/general base catalyzed process, which is kinetically indistinguishable from general acid catalysis.

The mechanism of 2a hydrolysis discussed herein is typical of electron-deficient imines and other iminoquinones. Thus, water addition to the protonated imine is rate determining and general-base catalyzed. The high reduction potential of 2a indicates it is an electron-deficient system.

Factors which are believed to influence the hydrolytic stability of 2a below pH 6 include its electron-deficient character as well as stabilization of the protonated imine by internal hydrogen bonding. The former results in a low $pK_a$ for acid dissociation of the protonated imine (~2.5) and, consequently, the presence of very little protonated species at neutrality. Internal hydrogen bonding interactions in the structure shown below diminishes the positive charge on the imine nitrogen and slows water addition. The $pK_a$ of $2aH^+$ (~2.5) and the slow rate of water addition to this species $(4.8 \times 10^{-2} s^{-1})$ indicate hydrolysis would only occur at $1.0 \times 10^{-6} s^{-1}$ at pH=7.0 ($t_{\frac{1}{2}}$~5 days).

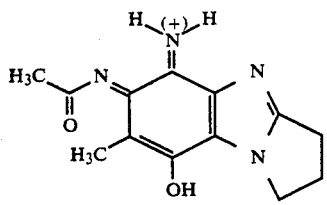

18

Evidence of internal hydrogen bonding involving the enolized amide nitrogen was obtained from thermodynamic studies of the syn/anti isomerization discussed hereinafter.

The kinetic and thermodynamic aspects of the syn-/anti isomerization process will now be considered.

Both general acid and general base catalysis are observed over the pH range where syn/anti imine isomerization occurs: $k(\text{acetate}) = 4.5 \times 10^{-3} M^{-1}s^{-1}$, $k(\text{monobasic phosphate}) = 4.21 \times 10^{-4} M^{-1}s^{-1}$, and $k(\text{dibasic phosphate}) = 1.71 \times 10^{-4} M^{-1}s^{-1}$. The presence of general catalysts suggests the isomerization mechanism involves prototropic shifts as shown in Equation 2. Others (See: McCarthy, C. G., *The Chemistry of the Carbon-Nitrogen Double Board;* Patai, S. editor; Interscience: N.Y., 1970, Chapter 9 and references cited therein) have also postulated the prototropic syn-/anti isomerization of unsubstituted imines.

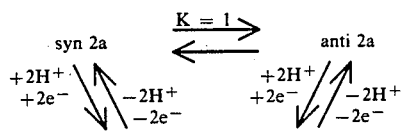

Equation 4

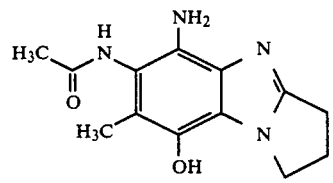

19

The thermoneutral syn/anti isomerization in aqueous buffer requires that the imino proton of anti 2a hydrogen bond to the nitrogen of the enolized acetamido group. In the absence of this hydrogen bond, syn 2a would likely be more stable than anti 2a in aqueous solution due to the presence of one or more internal hydrogen bonds in the former isomer (see syn 2a in Scheme 4). The $^1$H NMR and NOE studies of anti 2a in dimethyl sulfoxide-d$_6$ indicate enolization of the 6-acetamido group does not occur and syn 2a is more

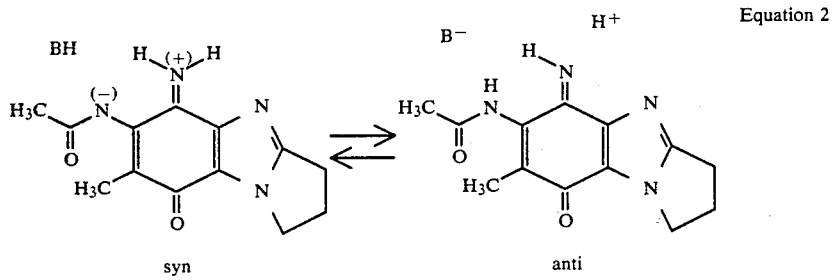

Equation 2

The Principle of Microreversibility requires general-base catalysis in one direction and general-acid catalysis in the opposite direction during the syn/anti equilibration process shown in Equation 2. The rate law for the equilibration process is thus shown in Equation 3.

$$k_{syn/anti} = k_1 + k_{-1} + k_{gb}[B] + k_{ga}[BH] \qquad \text{Equation 3}$$

wherein: $k_1$ and $k_{-1}$ (shown in Scheme 4, above) are water-catalyzed (lyate) rates and $k_{gb}$ and $k_{ga}$ are general base and general acid catalyzed rates, respectively. As required by Equation 3, equilibration actually involves both general acid and base catalysis.

The K value ($\sim 1$) for syn/anti isomerization of 2a in aqueous buffer was assessed from three thermodynamic cycles and from a product study. The results of the product study indicate K = 0.7. The two thermodynamic cycles shown in Scheme 4 indicate K = 1 to 2. These thermodynamic cycles were constructed by considering that protonation of syn/anti 2a provides the same cationic species 2aH$^+$ and that acid dissociation from syn/anti 2a probably provides the same anionic species 2aH$^-$. The third thermodynamic cycle was obtained by cyclic voltammetry; identical E values for both isomers indicate equilibration is a thermoneutral process, Equation 4.

stable than anti 2a in this solvent (K for syn/anti equilibration in this solvent is 15).

The iminoquinone hydrolytic studies demonstrate that internal hydrogen bonding is responsible for both the iminoquinone stability and the K value for syn/anti isomerization. Significantly, internal hydrogen bonding is also responsible for the hydrolytic stability of iminodaunomycin (See: Tong et al, op. cit.) as well as the electrochemical properties of other iminoquinones. (See: Amatore et al, *J. Electro anal. Chem.*, 1986, 207, 151).

Electrochemistry. Comparisons were made of the quinone and iminoquinone two-electron couples shown in chart 1. The oxygen reactivity of the respective reduced forms of these couples, 20 and 19, is also compared. It is concluded that the change from quinone to iminoquinone is accompanied by increases in reduction potential as well as decreases in the oxygen-mediated reoxidation rates of the reduced species.

CHART 1

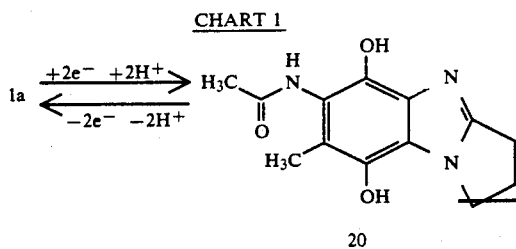

Nernst equation requires two more acid dissociations in the reduced species than the oxidized species. The p$K_a$ values of 1a/20 and of 2a/19 used in the Nernst fits are tabulated in Table 1. The p$K_a$ values, with error limits, were determined spectrophotometrically. Other p$K_a$ values, which fall outside the pH range studied, are approximated

TABLE I

| | p$K_a$ Values of 1a/20 and 20/19 Determined at 30° C. in $\mu$ = 1.0 (KCl) Buffer | | |
|---|---|---|---|
| entry | acid dissociation | acid species | p$K_a$ |
| 1 | 1aH$^+$ ⇌ 1a + H$^+$ | N(4) protonated quinone | 1.54 ± 0.06 |
| 2 | 1a ⇌ 1a$^-$ + H$^+$ | amide proton of quinone | 11.32 ± 0.13 |
| 3 | 20H$^+$ ⇌ 20 + H$^+$ | N(4)-protonated hydroquinone | 6.02 ± 0.20 |
| 4 | 20 ⇌ 20$^-$ + H$^+$ | 5-OH of hydroquinone | 11.11 ± 0.19 |
| 5 | 20$^-$ ⇌ 20$^{2-}$ + H$^+$ | 8-OH of hydroquinone | >14 |
| 6 | 20$^{2-}$ ⇌ 20$^{3-}$ + H$^+$ | amide proton of hydroquinone | >14 |
| 7 | 2aH$_2^{2+}$ ⇌ 2aH$^+$ + H$^+$ | N(4)-protonated iminoquinone | <0 |
| 8 | 2aH$^+$ ⇌ 2a + H$^+$ | protonated imino group | 2.6 ± 0.3 |
| 9 | 2a ⇌ 2a$^-$ + H$^+$ | amide proton of iminoquinone | 11.24 ± 0.01 |
| 10 | 19H$_2^+$ ⇌ 19H$^+$ + H$^+$ | N(4)-protonated aminophenol | 3.67 ± 0.16 |
| 11 | 19H$^+$ ⇌ 19 + H$^+$ | protonated 5-amino group | 9.44 ± 0.04 |
| 12 | 19 ⇌ 19$^-$ + H$^+$ | dissociation of hydroxyl, amide and amine protons | >15 |
| 13 | 19$^-$ ⇌ 19$^{2-}$ + H$^+$ | | >15 |
| 14 | 19$^{2-}$ ⇌ 19$^{3-}$ + H$^+$ | | >15 |

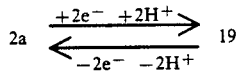

Quinone 1a and iminoquinone 2a two-electron reduction potentials were determined in anaerobic aqueous buffers ($\mu$=1, NaClO$_4$) at 25° C. over the pH range −1 to 10 employing conventional cyclic voltammetry. The working electrode was a graphite mull, the auxillary electrode was platinum, and the reference couple was Ag/AgCl. The voltammograms are quasireversible in character and also show a high degree of symmetry ($\alpha$~0.5).

Figure 2:
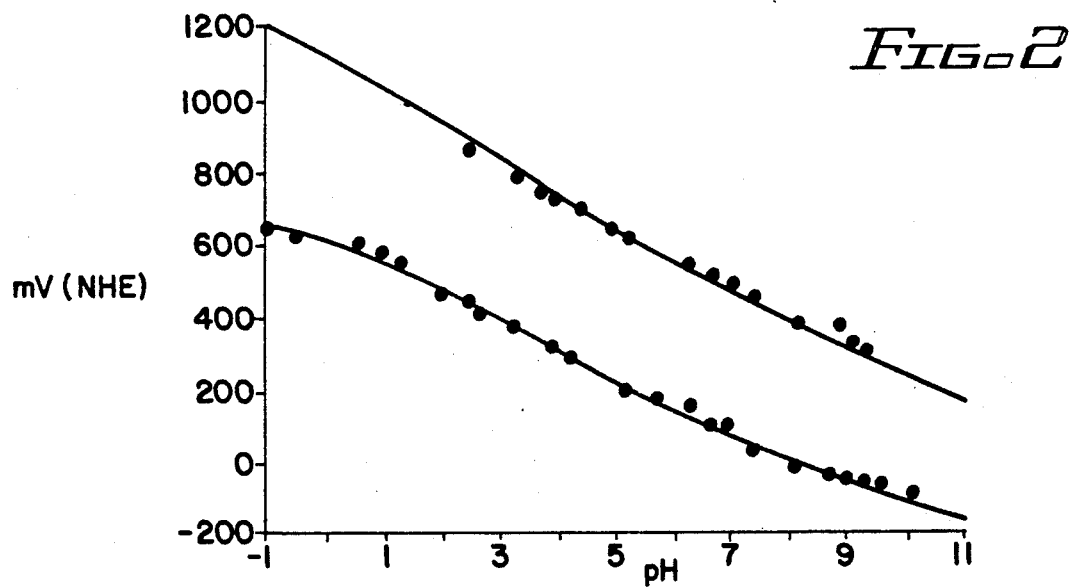
FIG. 2 shows $E_m$ vs pH data for the two-electron couples 2a/19 (plot B) and 1a/20 (plot A)

Voltammograms of the couple 1a/20 were obtained by scanning solutions of 1a in the cathodic and then anodic directions (300 mV s$^{-1}$). The quinone 1a is hydrolytically stable throughout the entire pH range studied and aqueous solutions could be prepared and degassed without appreciable decomposition. The iminoquinone 2a is hydrolytically stable at pH values ≧7 and voltammograms were also obtained by cathodic-anodic scanning of solutions of the oxidized species. Much below pH 6, 2a is rapidly hydrolyzed to the quinone and it was necessary to do anodic-cathodic scans on solutions of the acid-stable reduced species 19. Fast scans (>1000 mV s$^{-1}$) of acid solutions of 19 provided quasireversible voltammograms of 2a/19, even though 2a rapidly hydrolyses in these solutions FIG. 2 shows $E_m$ vs. pH data for both couples along with solid lines computer generated from the Nernst equation. Fitting the $E_m$ vs. pH data in FIG. 2 to the Nernst equation requires two more acid dissociations in the reduced species than the oxidized species. The p$K_a$ values of 1a/20 and of 2a/19 used in the Nernst fits are tabulated in Table 1. The p$K_a$ values, with error limits, were determined spectrophotometrically. Other p$K_a$ values, which fall outside the pH range studied, are approximated The Nernst fits in FIG. 2 show that the iminoquinone (Plot B) possesses much higher potentials than the quinone derivative (Plot A). For example, the $E_o$ value (reduction potential at pH=0) for 2a /19 is 1.11 V (NHE) and the $E_o$ value for 1a/20 is only 612 mV (NHE). Indeed, the iminoquinone even possesses an $E_o$ value greater than dichlorodicyanoquinone (DDQ) ($E_o$=946 mV, NHE). Like DDQ, 2a rapidly hydrolyses to a lower potential species (1a) in strong acid. Inspection for the p$K_a$ data in Table I reveals the reason of the high iminoquinone reduction potentials. Over the entire pH range studied, the iminoquinone couple 2a/19 is either diprotonated or monoprotonated whereas the quinone couple 1a/20 is either monoprotonated or neutral. Electron deficient couples, resulting from the presence of electron withdrawing groups or protonation, possess high reduction potentials.

In the absence of protic equilibria, iminoquinones should possess lower reduction potentials than quinones. This assessment is based on the lower electronegativity of nitrogen compared to oxygen. In fact, iminoanthraquinones possess lower reduction potentials for single electron transfer in aprotic solvent than the quinone analogues (See: Amatore et al, op. cit.).

The oxygen reactivity of 19 and 20 was studied in aerobic buffers ($\mu$=1.0, KCl) at 30° C. Both of these species are converted to the corresponding oxidized analogues, 2a and 1a, by first-order processes. Isolation studies and UV-visible spectra of completed reactions confirmed the formation of both analogues. As expected from the relative reduction potentials, the oxidation of 19 is slow enough to be studied up to pH=11 whereas the oxidation of 20 occurs at stopped-flow rates much above neutrality.

Figure 3:
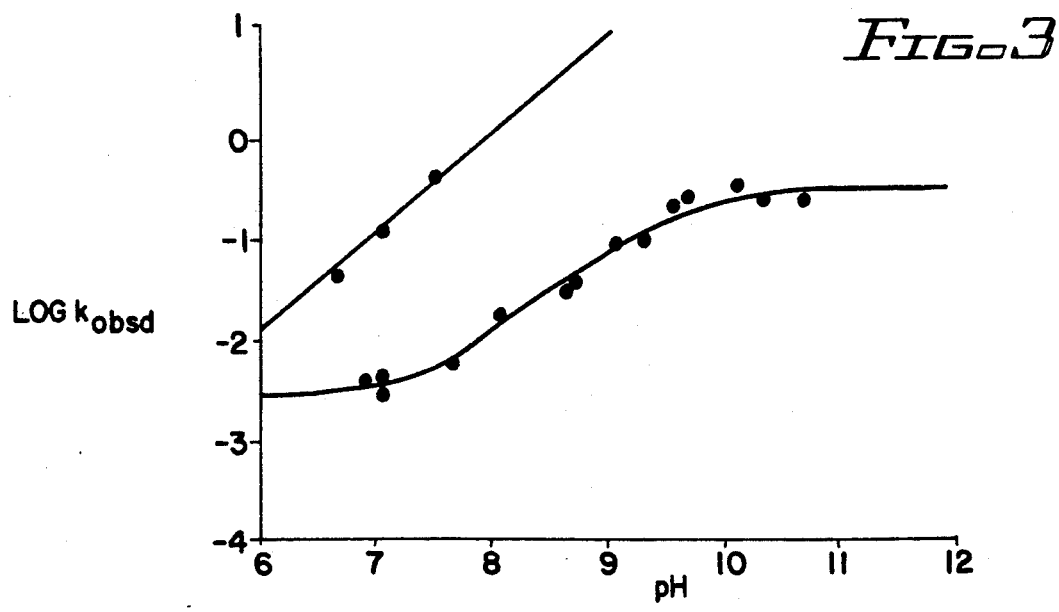
FIG. 3 shows plots of $k_{obsd}$ vs pH for the aerobic oxidation of 19 (plot B) and 20 (plot A) in aqueous buffer.

The pH profiles for the oxidation of 19 (Plot B) and 20 (Plot A) are shown in FIG. 3. The profile for the oxidation of 19 is consistent with oxidation of both the neutral species (19) and the monoprotonated species (19H+), see Scheme 5, below.

SCHEME 5

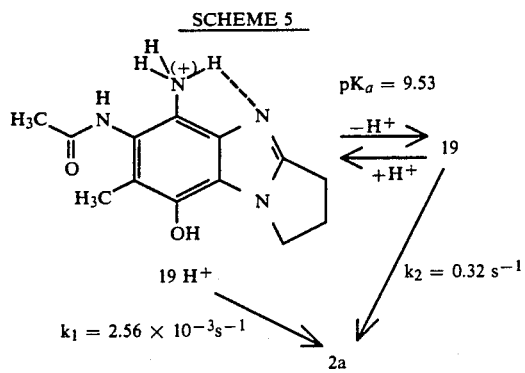

The rate law for the mechanism in Scheme 5 is found in Equation 5.

$$k_{obsd} = k_1 + \frac{k_2 K_a}{a_H + K_a} \qquad \text{Equation 5}$$

wherein: $k_1$ and $k_2$ are apparent first-order rate constants containing a term for the partial pressure of oxygen, $K_a$ is the acid dissociation constant of 19H+, and $a_H$ is the proton activity determined with a pH electrode. The solid curve of Plot B in FIG. 3 was computer generated with equation 5 using the values of the constants shown in Scheme 5. Consistent with the proposed mechanism, the kinetically-determined value of $K_a$ is nearly the same as the value determined spectrophotometrically (9.44, entry 11 of Table I). The greater oxygen reactivity of 19, compared to 19H+, is consistent with the decreasing $E_m$ values (i.e., decreasing stability of the reduced species) observed in the Nernst Fit (Plot B, FIG. 2) at pH values >6.

The oxidation rates of 20 increase with pH (slope of +1, Plot A of FIG. 3) and become too fast to measure above pH 7.5. In the pH range studied, 20 is largely in the neutral form with only small amounts of the hydroxyl anion 20− present (pK$_a$=11.11, Table I). The positive slope of Plot A may pertain to equilibrium formation of 20− (20⇌20− +H+) and rate-determining oxidation of this species. If this is the case, 20− is oxidized to 1a at 1566 s−1 in aerobic buffer.

Comparison of the pH profiles in FIG. 3 indicate 19 is oxidized about 100× slower than 20 at physiological pH (7.4). Thus, iminoquinone-based reductive alkylating agents should generate significantly less toxic oxygen species than quinone based agents.

Experimental Section

All analytically pure compounds were dried under high vacuum at room temperature or in a drying pistol heated with refluxing methanol. Compounds susceptible to decomposition (1c,d, 2, 19, 20) were not heated above room temperature. Some of the compounds still contained water of crystallization that was determined from the elemental analyses found. Experimental nitrogen percentages for 1c,d and syn 2a deviated from theoretical percentages by >0.5%. Repeat nitrogen analyses often showed a wide variation in percentage values; we believe this is due to incomplete combustion. 1H NMR and 13C NMR data and mass spectra (both the parent ion and fragmentation pattern) supported the assigned structures and TLC indicates these compounds are pure. No elemental analyses were obtained for anti 2a,b, 7c,d, 14, 19, 20; spectral data support the assigned structures and these compounds can be converted to well-characterized compounds.

Uncorrected melting and decomposition points were determined with a Mel-Temp apparatus. All TLC was run with Merck silica gel 60 (F$_{254}$) plates, employing a variety of solvents. IR spectra were taken as KBr pellets or thin films; the strongest IR absorbances are reported. 1H and 13C NMR spectra were obtained on a Bruker AM-400 spectrometer and chemical shifts are reported relative to TMS.

pK$_a$ constants were determined by spectrophotometric titration in μ=1.0 (KCl) aerobic aqueous solvent at 30°±0.2° C. with a Cary 15 outfitted with a titration cell. Acid dissociations from hydroquinones in strong base were measured under an argon atmosphere with Thunberg cuvettes. Details of the methodoloqy employed are found in a previous publication.

Kinetic Studies of Hydrolysis. The hydrolytic studies of 2a and the reoxidation studies of 19 and 20 were carried out in aerobic aqueous buffer at 30.0°±0.2° C. A dimethyl sulfoxide stock of the compound to be studied was prepared fresh and 50 μl of this stock was added to 2.95 mL of buffer. In the cases of 19 and 20, the dimethyl sulfoxide stock was kept under a blanket of argon. The absorbance vs time data were obtained on a Perkin-Elmer 559 or a Lambda-3 UV-vis spectrophotometer and fit to a first-order rate law.

Electrochemistry. The determination of $E_m$ values was carried out with a BAS 27 voltammograph. Measurements were carried out in μ=1.0 (NaClO$_4$) aqueous buffer at 25°-26° C. under an atmosphere of argon with a BAS Ag/AgCl gel electrode as reference. The electrode was calibrated against $E_o$ value of the benzoquinone/hydroquinone couple (699 mV, NHE). The midpoint potential $E_m$ was determined from the average of the anodic ($E_{p,a}$) and cathodic ($E_{p,c}$) potentials.

Nernst Fit. For each of the redox couples, 1a/20 and 2a/19, >20 $E_m$ determinations were made over the pH range studied. For each $E_m$ value of a couple, and $E_o$ value was calculated from the Nernst equation substituted with the acid dissociation constants in Table I and the proton activity determined with a pH meter. The average of all $E_o$ determinations was then substituted into the Nernst equation, with which the solid curve for the couple was generated.

Product Isolation of syn 2a Hydrolysis at pH 4. To a solution of 11 mg (0.042 mmol) of syn 2a in 1 mL of dimethyl sulfoxide was added 4 mL of pH 4 acetate buffer. The reaction mixture was stirred for 35 min at room temperature and then extracted 3× with 10 mL portions of chloroform. The dried extracts (sodium sulfate) were concentrated to a solid, which was recrystallized from chloroform/hexane, yield of 1a was 10 mg (90%). Identity as 1a was based on 1H NMR, mass spectral, and TLC data.

Product Isolation of syn 2a Reaction at pH 8. To a solution of 15 mg (0.058 mmol) of syn 2a in 1 mL of dimethyl sulfoxide was added 4 mL of pH 8 phosphate buffer. The reaction mixture was stirred at room temperature for 48 hours and then diluted with 10 mL of water and extracted 3× with 20 mL portions of chloroform. Concentration of the dried extracts (sodium sulfate) afforded 12 mg (80%) of a mixture of isomers: [syn/anti]=0.7 by $^1$H NMR.

Product Isolation of Aerobic Oxidation of 19. To a solution of 15 mg (0.057 mmol) of 19 in 0.5 mL of dimethyl sulfoxide was added 6.0 mL of pH 9 borate buffer. After the reaction was stirred at room temperature for 15 min, 10 mL of water was added and the diluted solution was extracted with 3×25 mL portions of chloroform. The dried extracts (sodium sulfate) were concentrated and the residue recrystallized from chloroform/hexane. Yield of a syn/anti mixture of 2a was 2 mg (33%). Identity was based on $^1$H NMR and mass spectral data.

Synthesis and Physical Properties of new compounds are provided below:

3-(N-pyrrolidino)-4-nitrotoluene (3). A mixture of 8.64 g (40 mmol) of 3-bromo-4-nitrotoluene and 8.5 g (120 mmol) of pyrrolidine was heated at reflux for 3 hours. The cooled reaction mixture was poured over 200 g of cracked ice and the resulting mixture extracted 2× with 200 mL portions of chloroform. The dried extracts (sodium sulfate) were concentrated to an oily residue, which was placed on a silica gel flash column. The product was eluted with hexane/chloroform (50:50). Evaporation of the eluant afforded an orange oil, which slowly solidified upon chilling in a refrigerator: yield 7.8 g (94%); mp 42° C.; TLC (CHCl$_3$), R$_f$=0.46; IR (film on NaCl) 1612, 1569, 1500, 1465, 1447, 1430, 1360, 1356, 1274, 600 cm$^{-1}$; NMR (CDCl$_3$) δ6.52 and 7.66 ( 2 H, ABX, J$_{ortho}$=8.24 Hz, J$_{meta}$=1.3 Hz, J$_{para}$~0 Hz, C(5) and C(6) aromatic protons, respectively), 6.69 (1 H, br s, C(2) aromatic proton), 3.20 (4 H, m, pyrrolidine methylenes adjacent to N), 2.34 (3 H, s, methyl), 1.97 (4 H, m, other pyrrolidine methylenes); mass spectrum (EI mode), m/z 206 (P+). Anal. Calcd for C$_{11}$H$_{14}$N$_2$O$_2$, C, 64.05; H, 6.84; N, 13.58. Found: C, 63.49; H, 6.73; N, 13.32.

7-Methyl-2,3-dihydro-1H-pyrrolo[1,2-a]benzimidazole-3-Acetate (4). A mixture consisting of 2.06 g (10 mmol) of 3, 1.36 g (10 mmol) of anhydrous ZnCl$_2$, and 10 mL of acetic anhydride was stirred at 100°-110° C. for 5 hours( or until 3 was no longer seen by TLC). The reaction mixture was poured into 10 mL of water and the black oil which formed was separated and evaporated to a small volume. The residue was combined with 20 mL of concentrated HCl and warmed to 80° C. for 5 min. Hydrogen sulfide gas was then passed into the HCl solution for 5 min followed by addition of NaOH until the pH=6.5-7.0. Extration of the above mixture with 3×50 mL portions of chloroform, drying the extracts (sodium sulfate), and chromatography on silica gel (column prepared with chloroform and the product eluted with chloroform/methanol [95:5]) afforded the 3-hydroxy derivative of 4 as a white powder: 1.00 g (52%) yield; mp 212° C.; TLC (chloroform/methanol [90:10]), R$_f$=0.52; IR (KBr pellet) 3135, 2861, 1524, 1445, 1350, 1322, 1298, 1290, 1092, 816 cm $^{-1}$;$^1$H NMR (dimethyl sulfoxide-d$_6$) δ7.46 and 6.98 (2 H, ABX system, J$_{ortho}$=8.2 Hz, J$_{meta}$=1.20 Hz; J$_{para}$~0 Hz, C(5) and C(6) protons, respectively), 7.26 (1 H, br s, C(8) proton), 5.78 (1 H, d, J=6.0 Hz, 3-hydroxyl proton), 5.05 (1 H, m, C(3) proton), 4.15 and 3.99 (2 H, 2×m, C(1) diastereomeric methylene), 2.88 and 2.36 (2 H, 2×m, C(2) diastereomeric methylene), 2.40 3 H, s, 7-methyl); mass spectrum (EI mode) m/z 188 (P+), 171 (P+-OH). Anal. Calcd for C$_{11}$H$_{12}$N$_2$O: C, 70.21; H, 6.38; N, 14.89. Found: C, 69.84; H, 6.33; N, 14.82.

Acetylation of the alcohol obtained above was carried out by stirring a mixture consisting of 376 mg (2 mmol) of the alcohol, 224 mg (2.07 mmol) of acetic anhydride, 122 mg (1 mmol) of (dimethylamino)pyridine, 220 mg (2.2 mmol) of triethylamine, and 20 mL of methylene chloride for 30 min at room temperature. The reaction mixture was then washed with water (3×25 mL) and dried over sodium sulfate. Evaporation of mixture to an oil and trituration with chloroform/hexane afforded 4 as a white solid; 391 mg (85%) yield; mp 154° C.; TLC (chloroform/methanol [90:10]), R$_f$=0.76; IR(KBr pellet) 1747, 1537, 1427, 1372, 1291, 1269, 1251, 1224, 1053, 808 cm$^{-1}$;$^1$H NMR (dimethyl sulfoxide-d$_6$) δ7.50 and 7.04 ( 2 H, ABX system, J$_{ortho}$=8.3 Hz, J$_{meta}$=1.3 Hz, J$_{para}$~0 Hz, C(5) and C(6) aromatic protons, respectively), 7.26 (1 H, br s, C(8) aromatic proton), 6.10 (1 H, dd, J=7.6 Hz, J=3.3 Hz, C(3) proton), 4.22 and 4.12 (2 H, 2×m, C(1) diastereomeric methylene), 3.10 and 2.56 (2 H, 2×m, C(2) diastereomeric methylene, 2.43 (3 H, s, 7-methyl), 2.07 (3 H, s, acetate methyl); mass spectrum (EI mode) m/z 230 (P+), 187 (P+-acetyl). Anal. Calcd for C$_{13}$H$_{14}$N$_2$O$_2$: C, 67.88; H, 6.12; N, 12.16. Found: C, 67.26; H, 5.99; N, 11.94.

6-Bromo-7-methyl-2,3-dihydro-1H-pyrrolo[1,2-a]benzimidazole-3-Acetate (5). To a solution of 500 mg (2.17 mmol) of 4 in 10 mL of glacial acetic acid, heated at 100° C., was added 3 mL of 0.72 M bromine in glacial acetic acid. After the addition, the reaction mixture was heated at 100°-110° C. for 4 hours. The cooled reaction mixture was diluted with 20 mL of water and then neutralized to pH 6.5 with aqueous sodium bicarbonate. The product crystallized from the solution as white crystals; yield upon drying the collected solid was 510 mg (75%). Recrystallization from chloroform/hexane afforded analytically pure material: dec pt 191° C.; TLC (chloroform/methanol [80:20]), R$_f$=0.64; IR (KBr pellet) 1748, 1531, 1455, 1424, 1371, 1288, 1249, 1082, 1051, 851 cm$^{-1}$; $^1$H NMR (dimethyl sulfoxide-d$_6$) δ7.86 and 7.58 ( 2 H, 2×s, aromatic protons), 6.11 ( 1 H, dd, J=7.6 Hz, J=3.2 Hz, C(3) proton coupled to C(2) methylene) 4.23 and 4.12 (2 H, 2×m, C(1) diastereomeric methylene) 3.12 and 2.52 (2 H, 2×m, C(2) diastereomeric methylene), 2.49 (3 H, s, 7-methyl), 2.07 (3 H, s, acetate methyl); mass spectrum (EI mode) m/z 308 and 310 (P+, $^{79}$Br and P+,$^{81}$Br), 265 and 267 (P+-acetyl) 249 and 251 (P+-acetic acid). Anal. Calcd for C$_{13}$H$_{13}$BrN$_2$O$_2$.0.25 C, 49.76; H, 4.25; N, 8.92. Found: C, 50.00; H, 4.20; N, 8.85

6-Bromo-7-methyl-5-nitro-2,3-dihydro-1H-pyrrolo[I,2-a]benzimidazole-3-Acetate (6). A solution of 500 mg (1.61 mmol) of 5 in 10 mL of a 9:1 mixture of fuming nitric acid and concentrated sulfuric acid was stirred in an ice bath for 10 min. The completed reaction was poured over cracked ice and the pH of the resulting solution adjusted to pH 6.5 with aqueous sodium bicarbonate. Extraction of this solution with 3×50 mL of chloroform, drying the extracts (sodium sulfate), and then concentration afforded a yellow oil. Dissolution of this oil in a small volume of chloroform and addition of hexane resulted crystallization of 6: 411 mg (71%) yield; dec pt 185° C.; TLC (chloroform/methanol [80:20]), R$_f$=0.73; IR (KBr pellet) 1747, 1539, 1488, 1442, 1374, 1350, 1305, 1232, 1089, 1044 cm$^{-1}$; $^1$H NMR (dimethyl sulfoxide-d$_6$) δ7.90 (1 H, s, aromatic), 6.15 (1 H, dd, J=7.7 Hz, J=3.2 Hz, C(3) proton coupled with C(2) methylene), 4.33 and 4.20 (2 H, 2×m, C(1) diastereomeric methylene), 3.15 and 2.60 (2 H, 2×m, C(2) diastereomeric methylene), 2.55 (3 H, s, 7-methyl), 2.09 (3 H, s, acetate methyl); mass spectrum (EI mode) m/z 353 and 355 (P+, $^{79}$Br and P+, $^{81}$Br), 310 and 312 (p+-acetyl), 293 and 295 (P+-acetic acid). Anal. Calcd for $C_{13}H_{12}BrN_3O_4$: C, 44.07; H, 3.41; N, 11.86. Found: C, 44.16; H, 3.27; N, 11.59.

6-Bromo-7-methyl-5-nitro-2,3-dihydro-1H-pyrrolo [1,2-a]benzimidazole-3-Carbamate (8). The conversion of 6 to 8 was carried out by the three-step process described below.

Deacetylation was carried out by suspending 200 mg (0.56 mmol) of 6 in 25 mL of methanol and then adding 31 mg of sodium methoxide. The reaction was stirred for 30 min at room temperature and the crystallized alcohol derivative filtered off; 142 mg (81%) yield. Recrystallization was carried out by dissolving the product in 15 mL of methanol-chloroform (1:4) and then adding a small amount of hexane followed by chilling: dec pt 255° C.; TLC (chloroform/methanol [90:10]), $R_f$=0.4; IR (KBr pellet) 3200, 1545, 1516, 1438, 1381, 1372, 1345, 1299, 1101 cm$^{-1}$; $^1$H NMR (dimethyl sulfoxide-d$_6$) δ7.83 (1 H, s, aromatic), 6.03 H, d, J=5.6 Hz, 3-hydroxyl), 5.13 ($^1$H, m, C(3) proton), 4.27 and 4.09 (2 H, 2×m, C(1)-diastereomeric protons), 2.94 and 2.41 (2 H, 2×x m, C(2)-diastereomeric protons), 2.53 (3 H, s, 7-methyl); mass spectrum (EI mode) m/z 311 and 313 (P+, $^{79}$Br and P+, $^{81}$Br) Anal. Calcd for $C_{11}H_{10}BrN_3O_3$: C, 42.31; H, 3.22; N, 13.46. Found: C, 42.44; H, 3.13; N, 13.34.

The phenyl carbonate derivative of the alcohol was prepared as described below. To a solution of the alcohol (400 mg, 1.27 mmol) in 20 mL of pyridine, chilled to 0° C., was added 400 μl of phenyl chloroformate. The reaction was stirred at 0° C. for 15 min and then at room temperature for 1 hour. The completed reaction was diluted with 150 mL of ethyl acetate and the resulting mixture extracted 3× with 50 mL of 20% acetic acid and then 2× with 50 mL of water. Drying of the extracts (sodium sulfate) and concentration afforded the carbonate as a light yellow solid; yield 450 mg (81%). Recrystallization was carried out from chloroform/hexane: mp 172°-175° C.; TLC (chloroform/methanol [90:10]), $R_f$=0.64; IR (KBr pellet) 1765, 1538, 1350, 1293, 1249, 1201, 1184, 1084, 946, 777 cm$^{-1}$; $^1$H NMR (dimethyl sulfoxide-d$_6$) δ7.94 (1 H, s, aromatic), 7.46 and 7.31 (5 H, 2×m, phenyl), 6.22 (1 H, dd, J=7.5 Hz, J=3.6 Hz, C(3) proton), 4.39 and 4.26 (2 H, 2×m, C(1) diastereomeric methylene), 3.24 and 2.85 (2 H, 2×m, C(2) diastereomeric methylene), 2.56 (3 H, s, 7-methyl); mass spectrum (EI mode) m/z 431 and 433 (P+, $^{79}$Br and P+, $^{81}$Br), 294 and 296 (P+-Ph—O—CO$_2$). Anal. Calcd for $C_{18}H_{14}BrN_3O_5$.0.25 H$_2$O: C, 49.49; H, 3.28; N, 9.61. Found: C, 49.62; H, 3.17; N, 9.51.

The preparation of the carbamate 8 was carried out by treatment of the carbonate derivative with ammonia. To 30 mL of anhydrous ammonia at −76° C. was added a solution of the carbonate, 211 mg (0.48 mmol), in 30 mL of dry dichloromethane. The solution was stirred at −76° C. for 30 min and the reaction then allowed to come to room temperature over a 3 hour period. The solvent was evaporated and the solid residue recrystallized from chloroform/hexane to afford yellow crystals of 8: dec pt 236° C.; TLC (chloroform/methanol [90:10]), $R_f$=0.4; IR (KBr pellet) 3372, 1715, 1533, 1416, 1400, 1378, 1370, 1335, 1300, 1094 cm$^{-1}$; $^1$H NMR (dimethyl sulfoxide-d$_6$) δ7.89 (1 H, s, aromatic), 6.82 and 6.73 (2 H, 2×br s, amide protons), 6.00 (1 H, dd, J=7.5 Hz, J=3.8 Hz, C(3) proton) 4.30 and 4.80 (2 H, 2×m, C(1) diastereomeric methylene) 3.13 and 2.55 (2 H, 2×m, C(2) diastereomeric methylene), 2.54 (3 H, s, 7-methyl); mass spectrum (EI mode) m/z 354 and 356 (P+, $^{79}$Br and P+, $^{81}$Br), 311 and 313 (P+- O=C=N—H), 293 and 295 (P+-carbamic acid). Anal. Calcd for $C_{12}H_{14}BrN_4O_2$: C, 40.58; H, 3.11; N, 15.77. Found: C, 40.61; H, 3.13; N, 15.41.

5-Amino-7-methyl-2,3-dihydro-1H-pyrrolo[1,2-a] benzimidazole 3-Acetate and 3-Carbamate (7c and 7d). A suspension of 6 or 8 in 100 mL of methanol containing 60 mg 5% Pd on charcoal was shaken under 50 psi H$_2$ for 6 hours. The reaction was filtered through Celite and the filter cake washed with methanol. Acidification of the filtrate with a few drops of 1 N HCl and evaporation in vacuo afforded the dihydrochloride salt of the amine. Recrystallization was carried out from ethyl acetate/methanol.

Reduction of 6 afforded an 80% yield of the dihydrochloride salt of 7c: dec pt 250° C.; TLC (chloroform/methanol [90:10]), $R_f$=0.67; IR (KBr pellet) 3384, 3313, 3205, 2853, 2836, 2752, 1750, 1643, 1494, 1218 cm$^{-1}$; $^1$H NMR (dimethyl sulfoxide-d$_6$) δ6.99 (1 H, s, C(8) proton), 6.73 (1 H, s, C(6) proton),6.25 (1 H, dd, J=7.9 Hz, J=3.7 Hz, C(3) proton, 4.40 and 4.26 (2 H, 2×m, C(1) diastereomeric methylene) 3.19 and 2.70 (2 H, 2×m, C(2) diastereomeric methylene), 2.38 (3 H, s, 7-methyl), 2.12 (3 H, s, acetate methyl); mass spectrum (EI mode) m/z 245 (P+ of base), 202 (P+-acetyl), 186 (P+-acetamide).

Reduction of 8 afforded an 87% yield of the dihydrochloride salt of 7d: dec pt 245° C.; TLC (chloroform/methanol [80:20]), $R_f$=0.48; IR (KBr pellet) 3315, 3270, 3200, 3146, 3041, 1736, 1402, 1370, 1318 cm$^{-1}$; $^1$H NMR (dimethyl sulfoxide-d$_6$) δ7.04 and 6.93 (2 H, 2×Br s, amide protons), 6.88 (1 H, s, C(8) proton), 6.64 (1 H, s, C(6) proton), 6.12 (1 H, dd, J=8.0 Hz, J=3.9 Hz, C(3) proton), 4.39 and 4.24 (2 H, 2×m, C(2) diastereomeric methylene), 3.22 and 2.65 (2 H, 2×m, C(2) diastereomeric methylene) 2.36 (2 H, s, 7-methyl); mass spectrum (EI mode) m/z 246 (P+), 202 (P+- O=C—NH$_2$), 185 (P+-carbamic acid).

7-Methyl-2,3-dihydro-1H-pyrrolo[I,2-a] benzimidazole-5,8-dione-3-Acetate and 3 Carbamate (9c and 9d). To a suspension of 0.35 mmol 7c or 7d in 10 mL of water containing 80 mg of monobasic potassium phosphate was added a solution of 500 mg of Fremy's salt in 50 mL of water containing 200 mg of monobasic potassium phosphate. The reaction mixture was stirred at room temperature for 1.5 hours and then extracted 5× with 20 mL of chloroform. The dried extracts (sodium sulfate) were concentrated to an oil and then flash chromatographed employing silica gel with acetone (9d) or chloroform (9c) as eluant. The product was recrystallized from acetone/hexane.

Oxidation of 7c afforded a 54% yield of 9c: mp 132°-135° C.; TLC (acetone), $R_f$=0.67; IR (KBr pellet) 1746, 1739, 1673, 1653, 1610, 1510, 1372, 1329, 1235, 1154 cm$^{-1}$; $^1$H NMR (CDCl$_3$) δ6.54 (1 H, q, J=1.2 Hz, C(6) proton), 6.09 (1 H, dd, J=7.6 Hz, J=2.9 Hz, C(3) proton), 4.40 and 4.31 (2 H, 2×m, C(1) diastereomeric methylene), 3.18 and 2.66 (2 H, 2×m, C(2) diastereomeric methylene) 2.11 (3 H, d, J=1.2 Hz, 7-methyl), 2.10 (3 H, s, acetate methyl): mass spectrum (EI mode) m/z 260 (P+), 217 (P+-acetyl), 200 (P+-acetic acid). Anal. Calcd for $C_{13}H_{12}N_2O_4$: C, 59.99; H, 4.64; N, 10.76. Found: C, 59.55; H, 4.70; N, 10.53.

Oxidation of 7d afforded a 58% yield of 9d: dec pt 201° C.; TLC (acetone), $R_f$=0.53; IR (KBr pellet) 3411, 1741, 1735, 1727, 1654, 1610, 1330, 1168, 1155, 1147 cm$^{-1}$; $^1$H NMR (CDCl) δ6.54 (1 H, q, J=~1 Hz, C(6) proton), 6.01 (1 H, dd, J=7.6 Hz, J=3.3 Hz, C(3) proton), 4.70 (2 H, br s, amide protons), 4.40 and 4.29 (2 H, 2×m, C(1) diastereomeric methylene) 3.17 and 2.73 (2 H, 2×m, C(2) diastereomeric methylene), 2.10 (3 H, d, J~1 Hz, 7-methyl); mass spectrum (EI mode) m/z 261 (P+), 217 (P+-O=C—NH$_2$), 201 (P+-carbamate). Anal. Calcd for C$_{12}$H$_{11}$N$_3$O$_4$: C, 55.17; H, 4.24; N, 16.08. Found: C, 55.65; H, 4.28; N, 16.26.

6-(N-aziridinyl)-7-methyl-2,3-dihydro-1H-pyrrolo [1,2-a]benzimidazole 5,8-dione-3-Acetate (1c). To a solution of 52 mg (0.2 mmol) of 9c in 2 mL of methanol, chilled at 0° C., was added 0.5 mL of ethyleneimine. After stirring at 0° C. for 30 min, the reaction was stirred at room temperature for 1 hour. The solvent was then removed in vacuo and the brick-red residue flash chromatographed on silica gel using chloroform as eluant. The purified product was recrystallized from methylene chloride/hexane: 25 mg
(42%) yield; mp 125°-127° C.; TLC (acetone), R$_f$=0.65; IR (KBr pellet) 1746, 1679, 1636, 1518, 1378, 1341, 1314, 1230, 1141, 1035 cm$^{-1}$; $^1$H NMR (CDCl$_3$) δ6.05 (1 H, dd, J=7.5 Hz, J=3 Hz, C(3) proton), 4.29 (2 H, m, C(1) diastereomeric methylene), 3.13 and 2.62 (2 H, 2×m, C(2) diastereomeric methylene), 2.36 (4 H, s, aziridine protons), 2.09 (3 H, s, 7-methyl), 2.07 (3 H, s, acetate methyl); $^{13}$C NMR (CDCl$_3$)δ178.0, 176.7, 169.9, 155.9, 153.1, 144.5, 130.3, 124.6, 66.4, 43.6, 35.0, 29.4, 20.8, 9.5 cps; mass spectrum (EI mode) m/z 301 (P+), 286 (P+-methyl), 258 (P+-acetyl). Anal. Calcd for C$_{15}$H$_{15}$N$_3$O$_4$; C, 59.79; H, 5.01; N, 13.94. Found: C, 59.65; H, 5.06; N, 12.96 to 13.28.

6-N-Aziridinyl-7-methyl-2,3-dihydro-1H-pyrrolo [1,2-a]benzimidazole-5,8-dione-3-Carbamate (1d). A solution of 26 mg (0.1 mmol) of 9d in 7 mL of methanol was combined with 0.25 mL of ethyleneimine and the mixture stirred at room temperature for 1.5 hours. The solvent was evaporated in vacuo and the red residue flash chromatographed on silica gel using acetone as eluant. The product was recrystallized from acetone/hexane 15 mg (50% yield; dec pt 185° C.; TLC (acetone), R$_f$=0.52; IR (KBr pellet), 3444, 3364, 1727, 1653, 1325, 1311 cm$^{-1}$; $^1$H NMR (CDCl$_3$) δ5.98 (1 H, dd, J=7.5 Hz, J=3 Hz, C(3) proton), 4.68 (2 H, br s, amide protons), 4.36 and 4.28 (2 H, 2×m, C(1) diastereomeric methylene), 3.15 and 2.71 (2 H, 2×m, C(2) diastereomeric methylene), 2.36 (4 H, s, aziridinyl protons), 2.08 (3 H, s, 7-methyl); $^{13}$C NMR (CDCl$_3$) δ178.0, 176.7, 156.0, 155.3, 153.0, 144.4, 130.3, 124.5, 67.2, 43.6, 35.1, 29.4, 9.5 cps; mass spectrum (EI mode) m/z 302 (P+), 259 (P+-O=C=N—H). Anal. Calcd for C$_{14}$H$_{14}$N$_4$O$_4$.0.5 H$_2$O: C, 54.01; H, 4.85; N, 17.99. Found: C, 54.03; H, 4.58; N, 16.81-6.70.

2,4-Dinitro-5-N-pyrrolidinotoluene (10). A mixture of 5-bromo-2,4-dinitrotoluene (2.61 g, 10 mmol) and pyrrolidine (2.49 g, 35 mmol) was heated at 90°-100° C. for 2 hours. The resulting dark brown oil was combined with cracked ice and the precipitated solids filtered off, washed with water, and vacuum dried. Purification was carried out by flash chromatography of the solids on a silica gel column using chloroform/hexane (50:50) as eluant. Evaporation of the eluants afforded 10 as orange needles: 2.0 g (82%) yield; mp 142° C.; TLC (chloroform), R$_f$=0.82; IR (KBr pellet) 1606, 1566, 1510, 1369, 1350, 1334, 1301, 1276, 1130, 833 cm$^{-1}$; $^1$H NMR (dimethyl sulfoxide-d$_6$) 8.83 and 8.53 (2 H, 2×s, aromatic protons), 3.27 (4 H, m, methylenes adjacent to pyrrolidine N), 2.61 (3 H, s, methyl), 1.99 (4 H, m, other pyrrolidine methylenes); mass spectrum (EI mode) m/z 251 (P+), 234 (P+-OH) Anal. Calcd for C$_{11}$H$_{13}$N$_3$O$_4$; C, 52.58; H, 5.21; N, 16.72. Found: C, 52.51; H, 5.27; N, 16.64.

2,4-Diacetamido-5-N-pyrrolidinotoluene (11). A suspension of 1.2 g (4.78 mmol) of 10 and 120 mg of 5% Pd on charcoal in 20 mL of methanol was shaken under 50 psi H$_2$ for 4 hours. The mixture was then filtered through Celite and the filtrate combined with 10 mL of acetic anhydride. After stirring this solution for 1 hour, the solvent was removed in vacuo and ether added to crystallize the residue. Yield of crude product, suitable for the next step, was 1.05 g (81%). An analytical sample was prepared by recrystallization from chloroform/hexane: dec pt 234° C.; TLC (chloroform/methanol [80:20]), R$_f$=0.61; IR (KBr pellet) 3261, 1651, 1616, 1526, 1491, 1464, 1454, 1416, 1368, 1280 cm$^{-1}$; $^1$H NMR (dimethyl sultoxide-d$_6$) δ9.11 and 9.02 (2 H, 2×s, amide protons), 7.21 and 6.65 (2 H, 2×s, aromatic protons), 3.11 (4 H, m, methylenes adjacent to pyrrolidine nitrogen), 2.09, 1.99, and 1.98 (9 H, 3×s, methyls), 1.84 (4 H, m, other pyrrolidine methylenes); mass spectrum (EI mode) m/z 275 (P+), 232 (P+-acetyl), 217 (P+-acetamido). Anal. Calcd for C$_{15}$H$_{21}$N$_3$O$_2$; C, 65.42; H, 7.68; N, 15.26. Found: C, 65.00; H, 7.68; N, 15.00.

7-Methyl-6-nitro-2,3-dihydro-1H-pyrrolo[,1,2-a] benzimidazole 3-Acetate (12). A mixture consisting of 2.5 g (10 mmol) of 10, 2.72 g (20 mmol) of ZnCl$_2$, and 10 mL of acetic anhydride was refluxed (90°-100° C.) for 4 hours. The reaction mixture was then cooled and combined with 100 mL of water. Extraction of the diluted reaction mixture with 3×50 mL portions of chloroform and concentration of the dried (sodium sulfate) extracts afforded crude product. Purification by silica gel chromatography, using ethyl acetate/methanol (95:5) as eluant, afforded pure 12 as a light yellow powder: 1.4 g (53%) yield; mp 172° C. dec; TLC (chloroform/methanol [90:10]) R$_f$=0.51; IR (KBr pellet) 1738, 1527, 1373, 1344, 1318, 1297, 1261, 1248, 1078, 1034 cm$^{-1}$; $^1$H NMR (dimethyl sulfoxide-d$_6$) δ8.48 (1 H, s, C(5) aromatic), 7.27 (1 H, s, C(8) aromatic), 6.20 (1 H, dd, J=7.6 Hz, J=3.8 Hz, C(3) proton), 4.31 and 4.17 (2 H, 2 m, C(1) diastereomeric methylene), 3.24 and 2.72 (2 H, 2 m, C(2) diastereomeric methylene), 2.72 (3 H, s, 7-methyl), 2.15 (3 H, s, acetate methyl); mass spectrum (EI mode), m/z 275 (P+), 258 (P+-OH), 232 (P+-acetyl). Anal. Calcd for C$_{13}$H$_{13}$N$_3$O$_4$; C, 56.67; H, 4.72; N, 15.27. Found: C, 56.61; H, 4.72; N, 14.97.

6 Acetamido-7-methyl-2,3-dihydro-1H-pyrrolo [1,2-a]benzimidazole (13). A mixture of 1 g (3.63 mmol) of 11, 6 mL of 96% formic acid, and 3 mL of 30% hydrogen peroxide was stirred at 70° C. for 30 min. The reaction mixture color changed from blue to red-brown, and finally to yellow upon completion. The reaction mixture was then diluted with water and neutralized to pH 7.00 with concentrated ammonium hydroxide. Extraction of the neutralized solution with 2×50 mL portions of chloroform, drying the extracts (sodium sulfate), and concentration afforded crude 13 as a yellow solid. Recrystallization was carried out from chloroform-hexane: 676 mg (81%) yield; dec pt 200° C.; TLC (chloroform/methanol [90:10]), R$_f$=0.42; IR (KBr pellet) 3442, 3230, 1668, 1526, 1476, 1456, 1423, 1309, 1304, 1283 cm$^{-1}$; $^1$H NMR (dimethyl sulfoxide-d$_6$) δ9.23 (1 H, s, amide proton), 7.45 and 7.23 (2 H, 2×s, aromatic protons), 4.04 (2 H, t, J~7 Hz, C(1) methylene), 2.91 (2 H, t, J~7 Hz, C(3) methylene), 2.61 (2 H, quintet, J~7 Hz, C(2) methylene), 2.26 (3 H, s, 7-methyl), 2.04 (3 H, s, acetate methyl); mass spectrum (EI mode) m/z 229 (P+), 187 (P+-ketene). Anal. Calcd for $C_{13}H_{15}N_3O.0.5$-$H_2O$: C, 65.47; H, 6.76; N, 17.62. Found: C, 65.90; H, 6.59; N, 17.75.

6-Acetamido-7-methyl-2,3-dihydro-1H-pyrrolo [1,2-a]benzimidazole-3-Acetate (14). A solution of 1.1 g (3.99 mmol) of 12 in 200 mL of methanol was shaken under 50 psi $H_2$ in the presence of 200 mg of 5% Pd on carbon for 4 hours. The completed reaction was filtered through Celite into a flask containing 2 mL of acetic acid. The filtrate was then evaporated in vacuo to an acetic acid/amine mixture, to which was added 6 mL of acetic anhydride. This mixture was stirred for 30 min at room temperature, and then diluted with 200 mL of diethyl ether. Pure 14 crystallized from the ether solution after chilling for several hours: 809 mg (70%) yield. Recrystallization was carried out from a large volume of hot ethyl acetate: dec pt 232° C.; TLC (1-butanol-acetic acid-water [5:2:3]), $R_f=0.4$; IR (KBr pellet) 3260, 1741, 1647, 1537, 1368, 1233, 1145, 1131 cm$^{-1}$; $^1$H NMR (dimethyl sulfoxide-$d_6$) $\delta$9.28 (1 H, s, amide proton), 7.57 and 7.37 (2 H, 2×s, aromatic protons), 6.10 (1 H, dd, J=7.6 Hz, J=3.2 Hz, C(3) proton), 4.22 and 4.12 (2 H, 2×m, C(1) diastereomeric methylene), 3.11 and 2.55 (2 H, 2×m, C(2) diastereomeric methylene), 2.29 (3 H, s, 7-methyl), 2.07 and 2.05 (6 H, 2×s, acetate and acetamido methyls).

6-Acetamido-7-methyl-5-nitro-2,3-dihydro-1H-pyrrolo[1,2-a]benzimidazole (15a). To a mixture of 5.4 mL of fuming nitric acid and 0.6 mL of concentrated sulfuric acid, chilled at 0° C., was added 600 mg (2.61 mmol) of 13. The reaction mixture was stirred at 0° C. for 5 min and then poured into a mixture of 20 g of cracked ice and 30 mL of chloroform. The mixture was neutralized with saturated aqueous sodium bicarbonate and vigorously stirred to extract the product into the chloroform layer. The chloroform layer was removed and the aqueous layer extracted with 3×30 mL portions of chloroform. Drying the combined chloroform extracts (sodium sulfate) and concentration afforded 15a as a yellow solid. Recrystallization was carried out from chloroform/hexane: 500 mg (69%) yield; m.p. 198° C.; TLC (chloroform/methanol [85:15]), $R_f=0.44$; IR (KBr pellet) 1689, 1525, 1517, 1492, 1459 1421, 1369, 1358, 1263, 1249 cm$^{-1}$; $^1$H NMR (CDCl$_3$) $\delta$7.89 (1 H, s, amide proton), 7.38 (1 H, s, C(8) proton), 4.14 (2 H, t, J=7.4 Hz, C(1) methylene), 3.14 (2 H, t, J=7.4 Hz, C(3) methylene), 2.78 (2 H, quintet, J=7.4 Hz, C(2) methylene), 2.41 (3 H, s, 7-methyl), 2.21 (3 H, s, acetamido methyl); mass spectrum (EI mode) m/z 274 (P+), 256 (P+-H$_2$O), 232 (P+-ketene), 228 (P+-NO$_2$). Anal. Calcd for $C_{13}H_{14}N_4O_3.1.5 H_2O$: C, 51.84; H, 4.68; N, 18.59. Found: C, 51.64; H, 4.68; N, 18.52.

6-Acetamido-7-methyl-5-nitro-2,3-dihydro-1H-pyrrolo[1,2-a]benzimidazole-3-Acetate (15b) mixture of 2 mL of fuming nitric acid and 0.8 mL of concentrated sulfuric acid, chilled in a dry-ice acetone bath, was added 400 mg (1.39 mmol) of 14 portionwise over a two min period. The reaction mixture was removed from the ice bath and stirred for 15 min while coming to room temperature and then poured into a mixture of 50 g ice and 50 mL of chloroform. Saturated sodium bicarbonate was added to the above mixture with vigorous stirring until the pH was neutral. The chloroform layer was separated and the aqueous layer extracted 2× with 50 chloroform. Drying the combined extracts (sodium sulfate), concentration to a residue, and trituration with ethyl acetate afforded crystalline 15b: 310 mg (67%) yield. Recrystallization was carried out from chloroform/hexane: mp 204° C.; TCL (chloroform/methanol [9:1]), $R_f=0.24$; IR (KBr pellet) 1750, 1681, 1528, 1370, 1360, 1270, 1083 cm$^{-1}$; $^1$H NMR (CDCl$_3$) $\delta$7.89 (1 H, s, amide proton), 7.47 (1 H, s, C(8) proton), 6.17 (1 H, dd, J=7.5 Hz, J=3.5 Hz, C(3) proton), 4.2 (2 H, m, C(1) diastereomeric methylene), 3.17 and 2.72 (2 H, 2×m, C(2) diastereomeric methylene), 2.43 (3 H, s, 7-methyl) 2.22 and 2.13 (6 H, 2×s, acetate and acetamido protons); mass spectrum (EI mode) m/z 332 (P+), 314 (P+-H$_2$O), 286 (P+-NO$_2$). Calcd for $C_{15}H_{16}N_4O_5.0.25 H_2O$: C, 53.49; H, 4.93; N, 16.62. Found: C, 53.78; H, 4.62; N, 16.42.

7-Acetamido-5-amino-7-methyl-2,3-dihydro-1H-pyrrolo[1,2-a]benzimidazole (16a) and the 3-Acetate Derivative (16b). A solution of 1.2 mmol of 15a or 15b in 60 mL of methanol was shaken under 50 psi $H_2$ in the presence of 40 mg of 5% Pd on carbon for 2.5 hours. The catalyst was removed by filtration through Celite and the filtrate concentrated to a yellow oil. Dissolution of the oil in 15 mL of chloroform, addition of hexane until the solution became cloudy, and then chilling afforded the amine as a white crystalline solid.

Reduction of 15a afforded 15b in 74% yield: dec pt 235° C.; TLC ( chloroform/methanol [8:2]), $R_f=0.58$; IR (KBr pellet) 3362, 3216, 3209, 1669, 1634, 1552, 1533, 1305, 1297, 1277 cm$^{-1}$; $^1$H NMR (dimethyl sulfoxide-$d_6$) $\delta$9.10 (1 H, s, amide proton), 6.76 (1 H, s, C(8) proton), 4.23 (2 H, t, J=7.2 Hz, C(1) methylene), 3.28 (2 H, t, J=7.6 Hz, C(3) methylene), 2.74 (2 H, quintet, J~7.4 Hz, C(2) methylene), 2.18 (3 H, s, 7-methyl), 2.03 (3 H, s, acetate methyl); mass spectrum (EI mode) m/z 244 (P+), 229 (P+-methyl), 201 (P+-acetyl). Anal. Calcd for $C_{13}H_{16}N_4O.0.6 H_2O$: C, 61.21; H, 6.79; N, 21.95. Found: C, 61.13; H, 6.13; N, 21. 49.

Reduction of 15b afforded 16b in 77% yield: dec pt. 211° C.; TLC (chloroform/methanol [80:20]), $R_f=0.48$; IR (KBr pellet) 3440, 3399, 1738, 1663, 1620, 1491, 1235 cm$^{-1}$; $^1$H NMR (dimethyl sulfoxide-$d_6$) $\delta$8.89 (1H, s, amide proton), 6.64 (1H, s, C(8) proton), 6.08 (1 H, dd, J=7.5 Hz, J=3 Hz, C(3) proton), 4.96 (2 H, br s, amine protons), 4.14 and 4.05 (2 H, 2×m, C(1) diasteromeric methylene), 2.16 (3 H, s, 7-methyl), 2.06 and 2.04 (6 H, 2×s, acetate and acetamido methyls); mass spectrum (EI mode) m/z 302 (P+). Anal. Calcd for $C_{15}H_{18}N_4O_3$ $0.5.H_2O$: C, 58.30; H, 6.15; N, 17.98. Found: C, 58.61; H, 5.78; N, 17.76.

6-Acetamido-7-methyl-2,3-dihydro-1H-pyrrolo [1,2-a]benzimidazole-5,8-dione (1a) and the 3-Acetate Derivative (1b). To a suspension of 16a or 16b (0.7 mmol) in 10 mL of water, containing 200 mg of potassium phosphate monobasic, was added a solution of 1 g of Fremy's salt in 30 mL of water containing 500 mg of potassium phosphate monobasic. The mixture was stirred at room temperature for 2.5 hours and then extracted 3× with 100 mL portions of chloroform. The dried extracts (sodium sulfate) were concentrated to a yellow solid, which was recrystallized from chloroform/hexane.

Oxidation of 16a afforded 1a in 71% yield: dec pt 194° C.; TLC (acetone), $R_f=0.41$; IR (KBr pellet) 2860, 1651, 1539, 1518, 1485, 1466, 1310, 1279, 1245, 1099 cm$^{-1}$; $^1$H NMR (CDCl$_3$) $\delta$7.70 (1 H, br s, amide proton), 4.24 (2 H, t, J=7.0 Hz, C(1) methylene), 2.84 (4 H, m, C(2) and C(3) methylenes), 2.24 (3 H, s, 7-methyl), 1.96 (3 H, s, acetamido methyl); $^{13}$C NMR (CDCl$_3$) $\delta$178.0, 177.7, 167.6, 160.9, 143.9, 135.9, 131.1, 130.6, 45.2, 26.5, 24.2, 22.8, 13.5 cps; mass spectrum (EI mode) m/z 259 (P+), 244 (P+-methyl), 217 (P+-ketene). Anal. Calcd for $C_{13}H_{13}N_3O_3$: C, 60.22; H, 5.05; N, 16.20. Found: C, 60.04; H, 4.98; N, 15.93.

Oxidation of 16b afforded 1b in 27% yield: dec pt 221° C.; TLC (acetone), $R_f$=0.56; IR (KBr pellet) 1730, 1695, 1659, 1610, 1520, 1371, 1314, 1284, 1244, 1083; $^1$H NMR (CDCl$_3$) δ7.69 (1 H, br s, amide proton), 6.09 (1 H, dd, J=7.7 Hz, J=3.3 Hz, C(3)-proton), 4.37 (2 H, m, C(1) diastereomeric methylene), 3.18 and 2.72 (2 H, 2×m, C(2) diastereomeric methylene), 2.25 (3 H, s, 7-methyl), 2.10 and 1.98 (6 H, 2×s, acetate and acetamido methyls); $^{13}$C NMR (dimethyl sulfoxide-d$_6$) δ177.3, 176.6, 169.5, 167.9, 156.8, 143.9, 138, 133.5, 129.9, 66.3, 43.5, 34.0, 22.9, 20.5, 12.2 cps; mass spectrum (EI mode) m/z 317 (P+), 300 (P+-OH), 275 (P+-ketene). Anal. Calcd for $C_{15}H_{15}N_3O_5$: C, 56.78; H, 4.76; N, 13.27. Found: C, 56.59; H, 4.67; N, 12.87.

syn/anti 6-Acetamido-5-imino-7-methyl-2,3-dihydro-1H-pyrrolo[1,2-a]benzimidazol-8-one (2a). To a suspension of 100 mg (0.4 mmol) of 16a in 10 mL of 0.2 M pH 7.0 phosphate buffer (μ=1.0, KCl) was added a suspension of 500 mg of Fremy's salt in 20 mL of the same buffer. To assist in dissolution of the Fremy's salt, 20 mL of water was then added to the above mixture. While stirring the mixture at room temperature, purple syn 2a crystallized from solution. After 30 min, the syn 2a was filtered off and dried: 69 mg (65%) yield. The filtrate was extracted with 2×50 mL of chloroform to remove the anti isomer. Drying the extracts (sodium sulfate), evaporation to a solid residue, and finally recrystallization from chloroform/hexane afforded 10 mg (9.5%) of yellow anti 2a. Extensive purification of either isomer was not possible due to syn/anti interconversion in many solvents.

Physical properties of syn 2a: dec pt 260° C.; TLC (chloroform/methanol [90:10]), $R_f$=0.44; IR (KBr) 3250, 1652, 1625, 1608, 1422, 1393 cm$^{-1}$; $^1$H NMR (dimethyl sulfoxide-6) δ9.19 and 6.62 (2 H, 2×br s, imine protons, see Scheme 3), 4.12 (2 H, m, C(1) methylene), 2.81 and 2.58 (4 H, 2×m, C(2) and C(3) methylenes), 1.72 and 1.58 (6 H, 2×s, 7-methyl and acetamido methyls); $^{13}$C NMR (dimethyl sulfoxide-d$_6$) δ176.5, 158.6, 154.3, 149.5, 138.8, 129.8, 110.4, 96.2, 44.5, 26.1, 25.7, 22.2, 8.7 cps; mass spectrum (EI mode) m/z 258 (P+), 243 (P+-methyl), 229 (P+-C≡NH), 215 (P+-acetyl) Anal. Calcd for $C_{13}H_{14}N_4O_2 \cdot 1.25 H_2O$: C, 55.60; H, 5.69; N, 19.95. Found: C, 55.35; H, 5.12; N, 19.07.

Physical properties of anti 2a: dec pt 245° C.; TLC, same as syn 2a; IR (KBr pellet) 3260, 3200, 1683, 1644, 1625, 1504, 1484, 1465, 1422, 1341, 1314, 1252 cm$^{-1}$; $^1$H NMR (dimethyl sulfoxide-d$_6$) δ11.42 (1 H, s, imine proton), 9.57 (1 H, s, amide proton), 4.19 (2 H, t, J=6.8 Hz, C(1) methylene), 2.73 (4 H, m, C(2) and C(3) methylenes), 2.07 and 1.81 (6 H, 2×s, 7-methyl and acetamido methyl); mass spectrum (same as syn 2a).

syn/anti 6-Acetamido-5-imino-7-methyl-2,3-dihydro-1H-pyrrolo[1,2-a]benzimidazol-8-one-3-Acetate (2b). To a solution of 16b, 150 mg (0.49 mmol), in 25 mL of 0.2 M pH 7.0 phosphate buffer (μ=1.0, KCl) was added 708 mg of Fremy's salt. The mixture was stirred at room temperature for 1 hour, during which time red syn 2b crystallized from solution. Filtration, washing the solids with a small volume of water, and then drying afforded syn 2b as a fiberous red solid: 61 mg (36%) yield. The filtrate was extracted with 2×50 mL of chloroform. Evaporation of the dried extracts (MgSO$_4$) to a residue and then trituration with acetone afforded yellow anti 2b (21 mg (12%) yield).

Physical properties of syn 2b: dec pt 312° C.; TLC (acetone), $R_f$=0.57; IR (KBr pellet) 3340, 1745, 1625, 1601, 1380, 1238 cm$^{-1}$; $^1$H NMR (dimethyl sulfoxide-d$_6$) δ9.34 and 6.68 (2 H, 2×br s, imine protons), 5.99 (1 H, m, C(3) proton), 4.24 (2 H, m, C(1) diastereomeric methylene), 3.04 and ~2.5 (2 H, 2×m, C(2) diastereomeric methylene), 2.07 (3 H, s, 7-methyl), 1.74 and 1.54 (6 H, 2×s, acetate and acetamido methyls); $^{13}$C NMR (dimethyl sulfoxide-d$_6$) δ176.2, 169.6, 154.7, 154.1, 149.8, 138.7, 130, 110.6, 96.8, 65.5, 43.3, 34.1, 25.5, 20.6, 8.7 Cps; mass spectrum (EI mode) m/z 316 (P+). Anal. Calcd for $C_{15}H_{16}N_4O_4 \cdot 0.25 H_2O$: C, 56.15; H, 5.18; N, 17.45. Found: C, 55.94; H, 5.19; N, 17.18.

Physical properties of anti 2b: dec pt 304° C.; TLC (same as syn 2b); IR (KBr pellet) 3188, 1740, 1714, 1644, 1627, 1487, 1376, 1310, 1230 cm$^{-1}$; $^1$H NMR (dimethyl sulfoxide-d$_6$) δ11.65 (1 H, s, amide proton), 9.64 (1 H, s, imine proton), 6.06 (1 H, dd, J=8 Hz, J=3.8 Hz, C(3) proton), 4.29 (2 H, m C(1) diastereomeric methylene), 2.08 (6 H, 2×s) and 1.8 (3 H, s), 7-methyl, acetamido and acetate methyls, no assignments made; mass spectrum (same as syn 2a).

6-Acetamido-5-amino-8-hydroxy-7-methyl-2,3-dihydro-1H-pyrrolo[1,2-a]benzimidazole (19). A solution of 25 mg (0.09 mmol) of syn 2a in 5 mL of methanol was shaken under 50 psi H$_2$ in the presence of 5 mg of 5% Pd on charcoal. The catalyst was then removed by filtering through Celite and the filtrate immediately concentrated to a solid. Dissolution of the solid in 5 mL of chloroform/methanol (1:4) and adding hexane resulted in precipitation of 19: 20 mg (79%) yield; TLC (chloroform/methanol [6:4]), $R_f$=0.4; IR (KBr pellet) 3322, 3210, 3140, 1660, 1640, 1505 cm$^{-1}$; $^1$H NMR (dimethyl sulfoxide-d$_6$) δ9.19 (1 H, s, amide proton), 8.68 (1 H, s, 8-hydroxyl), 4.14 (2 H, t, J=7.1 Hz, C(1) methylene), 3.20 (2 H, t, J=7.5 Hz, C(3) methylene), 2.72 (2 H, m, C(2) methylene), 2.07 and 2.04 (6 H, 2×s, 7-methyl and acetammido methyl); mass spectrum (EI mode) m/z 260 (P+), 242 (P+-H$_2$O), 217 (P+-acetyl).

6-Acetamido-5,6-dihydroxy-7-methyl-2,3-dihydro-1H-pyrrolo[1,2-a]benzimidazole (20). A solution of 30 mg (0.11 mmol) of 1a in 10 mL of methanol was shaken under 50 psi H$_2$ for 25 min in the presence of 8 mg of 5% Pd on charcoal. After addition of 3 drops of concentrated HCl to the reaction, the catalyst was removed by filtering through Celite and the filtrate concentrated to a solid. Recrystallization of the solid by dissolution in a minimal amount of methanol followed by addition of ethyl acetate afford 20 as the HCl salt: 32 mg (97%) yield; TLC (chloroform/methanol [6:4]), $R_f$=0.57; IR (KBr pellet) 3337, 3150, 1650, 1505, 1299 cm$^{-1}$; $^1$H NMR (dimethyl sulfoxide-d$_6$) δ9.39 (2 H, s, 5,8-dihydroxy), 9.03 (1 H, s, amide proton), 4.45 (2 H, t, J=6.9 Hz, C(1) methylene), 3.22 (2 H, t, J=7.5 Hz, C(3) methylene), 2.72 (2 H, quintet, J=7.6 Hz, C(2) methylene), 2.10 and 2.08 (6 H, 2×s, 7-methyl and acetamido methyl); mass spectrum (EI mode) m/z 261 (P+), 243 (P+-H$_2$O), 219 (P+-ketene).

The azamitosenes and iminoazamitosenes of the present invention can be prepared by alternate procedures as will be discerned from the following description when read in conjunction with Schemes 6-8, as shown.

SCHEME 6
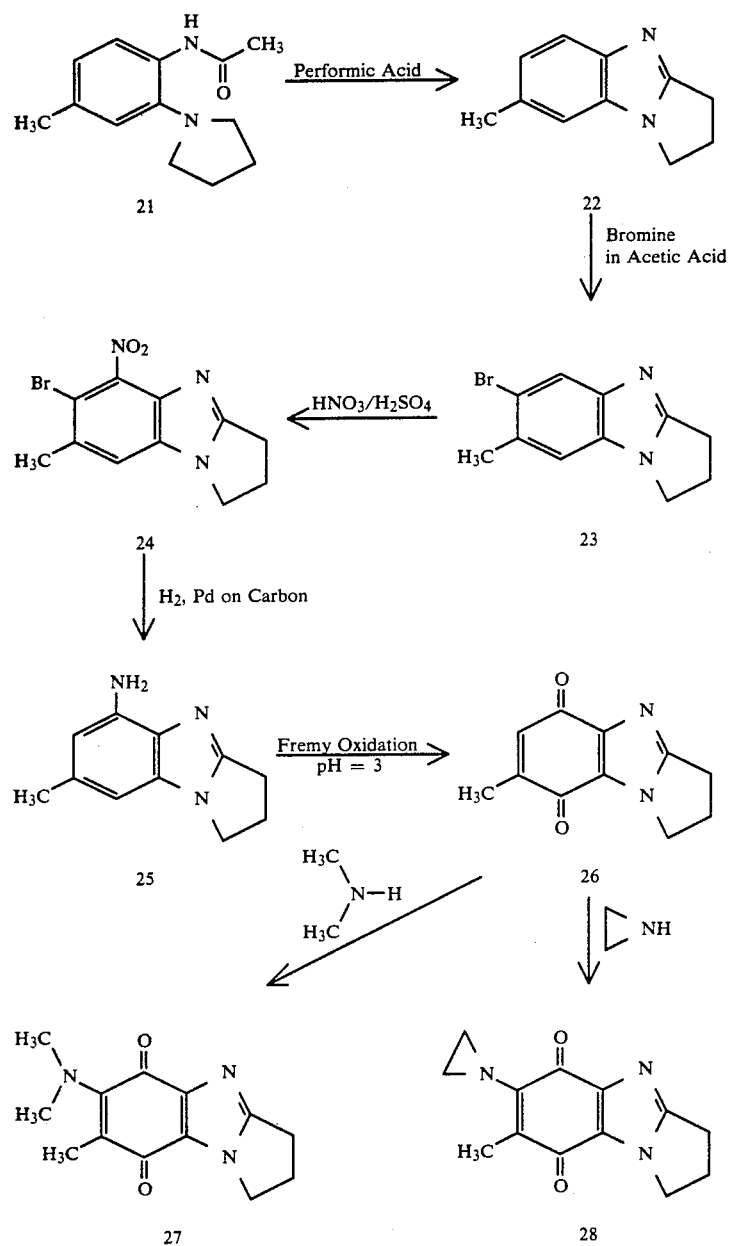
SCHEME 7
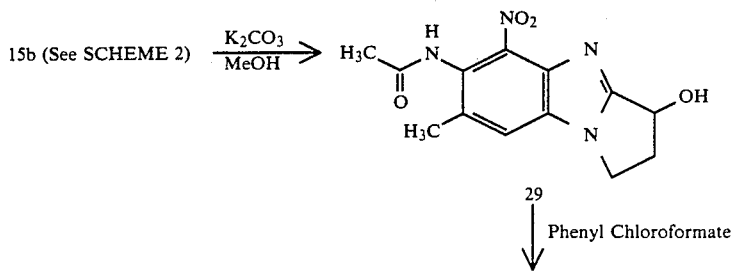

-continued
SCHEME 7

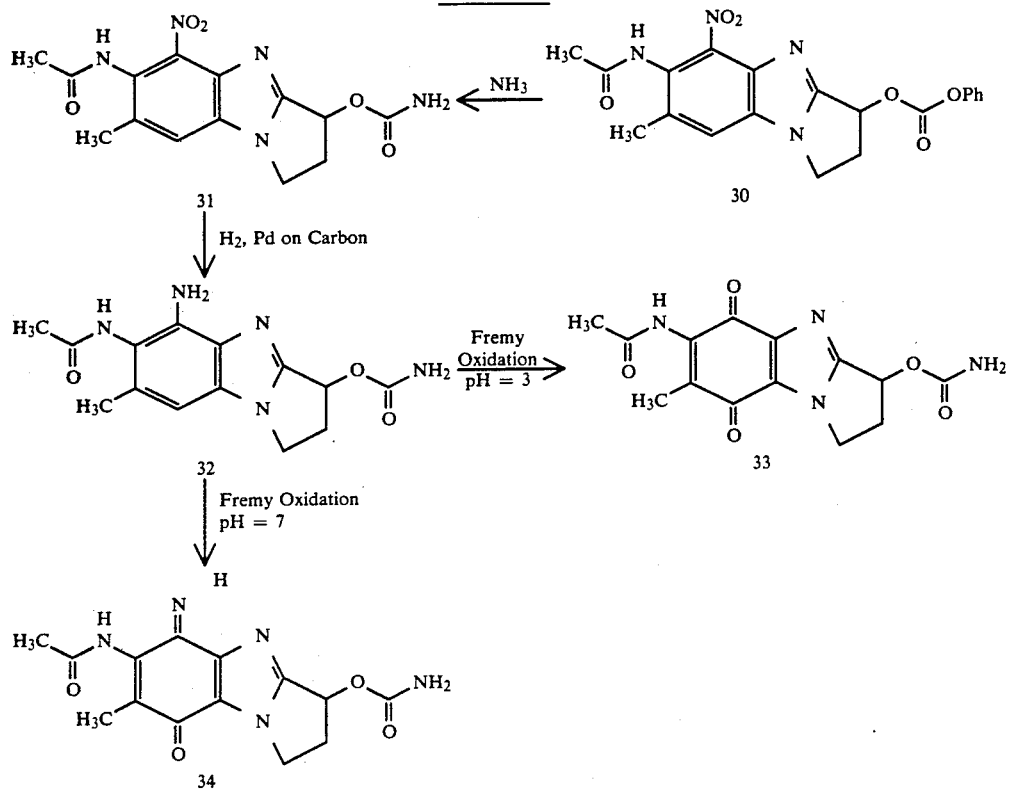

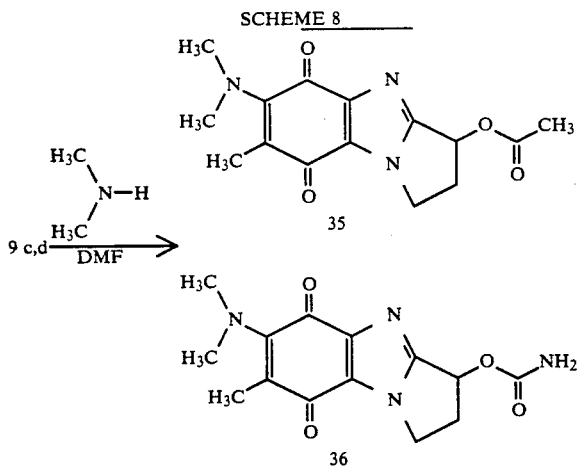

4-Acetamido-5-(N-pyrrolidino)toluene (21). A mixture consisting of 6.2 g (30.09 mmol) of 3-(N-pyrrolidino)-4-nitrotoluene, 500 mg of 5% Pd/C, and 250 mL of methanol was shaken under 50 psi for 4 hour. The completed reaction was filtered through Celite into a flask containing 10 mL of acetic acid. The filtrate was then evaporated in vacuo to an acetic acid/amine mixture, to which was added 10 mL of acetic anhydride. The mixture was stirred at room temperature and then diluted with 300 mL of diethyl ether. Pure product crystallized from the mixture after sonication and then chilling overnight, 5.46 g (83%) yield. Recrystallization was carried out from chloroform/hexane: m.p. 92°–94° C.; TLC (chloroform) $R_f$=0.75; IR(KBr pellet) 1655, 1644, 1605, 1534, 1509, 1489, 1418, 1373, 1355, 1329 cm$^{-1}$; $^1$H NMR (dimethyl sulfoxide-d$_6$) δ9.03 (1 H, s, amide proton), 7.05 and 6.57 (2 H, ABX, $J_{ortho}$=7.8 Hz, $J_{meta}$=0 Hz, $J_{para}$=0 Hz, C(5) and C(6) protons), 6.62 (1 H, s, C(2) proton), 3.14 (4 H, m, pyrrolidine methylenes adjacent to N), 2.21 (3 H, s, methyl), 1.98 (3 H, s, acetamido methyl), 1.84 (4 H, m, other pyrrolidine methylenes); mass spectrum (EI mode) m/z 218(P+), 175(P+-acetyl). Anal Calcd for C$_{13}$H$_{18}$N$_2$O: C, 71.52; H, 8.31; N, 12.83. Found: C, 71.28; H, 8.19; N, 12.95.

7-Methyl-2,3-dihydro-1H-pyrrolo[1,2-a] benzimidazole (22). A mixture consisting of 1.0 g (4.58 mmol) of 21, 3 mL of 96% formic acid, and 1.5 mL of 30% H$_2$O$_2$ was stirred at 70° for 40 min. The yellow-colored reaction mixture was then cooled to room temperature, diluted with water, and neutralized to pH 7.00 with concentrated ammonium hydroxide. Extraction of the neutralized solution with 3×100 ml portions of chloroform, drying the extracts (sodium sulfate), and concentration of the extracts afforded a yellowish-brown crude solid. Chromatography on silica gel employing 80:20 chloroform/hexane as the eluant afforded a white colored solid: 550 mg (69%) yield. An analytical sample was prepared by crystallization from diethyl ether/hexane: mp 118°–120° C.; TLC (chloroform), $R_f$=0.66, IR(KBr pellet), 2980, 1524, 1486, 1463, 1452, 1418, 1293, 1281, 1218, 803 cm$^{-1}$. $^1$H NMR (dimethyl sulfoxide-d$_6$) δ7.36, and 6.72 (2 H, ABX, $J_{ortho}$=8.2 Hz, $J_{meta}$=0 Hz, $J_{para}$=0 Hz, C(5) and C(6) aromatic protons respectively); 7.20 (1 H, s, C(8) proton), 4.04 (2 H, t, J~7 Hz, C(1) methylene), 2.90 (2 H, t, J~7.00 Hz, C(3) methylene), 2.61 (2 H, quintet, J~7 Hz, C(2) methylene), 2.40 (3 H, s, 7-methyl); mass spectrum (EI mode) m/z 172 (P+). Anal. Calcd for C$_{11}$H$_{12}$N$_2$: C, 72.91; H, 6.62; N, 15.45. Found: C, 73.31; H, 6.50; N, 15.34.

6-Bromo-7-methyl-2,3-dihydro-1H-pyrrolo[1,2-a] benzimidazole (23). To a solution of 1 q (5.81 mmol) of 22 in 30 mL of glacial acetic acid, heated at 100°, was added 300 μl of bromine in 3 mL glacial acetic acid. After the addition, the reaction mixture was heated at 100°-110° C. for 4 hours. The cooled reaction mixture was diluted with 100 mL of water and neutralized with aqueous sodium bicarbonate. The product crystallized from solution as a light yellow solid. Yield upon drying the collected solid Was 1.37 g (88%). Recrystallization from chloroform/hexane afforded analytically pure 23: mp 167°-170° C.; TLC (chloroform/methanol, [90:10]), $R_f=0.56$, IR(KBr pellet), 2949, 2929, 1581, 1521, 1482, 1461, 1448, 1418, 1291, 872 cm$^{-1}$; $^1$H NMR (dimethyl sulfoxide-d$_6$) δ7l, and 7.43 (2 H, 2×s, aromatic protons), 4.04 (2 H, t, J~7 Hz, C(1) methylene), 2.91 (2 H, t, J~7 Hz), C(3) methylene), 2.59 (2 H, quintet, J~7 Hz, C(2) methylene), 2.39 (3 H, s, 7-methyl); mass spectrum (EI mode) m/z 250 and 252 (P+, $^{79}$Br and P+, $^{81}$Br), 171 (P+-Br). Anal. Calcd for $C_{11}H_{11}BrN_2.0.25 H_2O$: C, 51.47; H, 4.31; N, 10.91. Found: C, 51.56; H, 4.24; N, 10.78.

6-Bromo-7-methyl-5-nitro-2,3-dihydro-1H-pyrrolo [1,2-a]benzimidazole (24). A solution of 245 mg (0.97 mmol) of 23 in a 5 mL mixture of fuming nitric acid and concentrated sulphuric acid (4:1) was stirred in an ice bath for 10 min. The completed reaction was poured over cracked ice and the pH of resulting solution adjusted to 6.5 with aqueous sodium bicarbonate. Extraction of this solution with 3×50 mL portions of chloroform, drying the extracts (sodium sulfate), and then concentration afforded a yellow solid, 165 mg (57%). Recrystallization from chloroform/hexane afforded analytically pure material: mp 201°-203° C.; TLC (chloroform/methanol, [95:5]) $R_f=0.61$; IR(KBr pellet) 1537, 1517, 1449, 1413, 1383, 1374, 1342, 1297, 884, 860 cm$^{-1}$; $^1$H NMR (dimethyl sulfoxide-d$_6$) δ7.77 (1 H, s, aromatic proton), 4.15 (2 H, t, J~Hz, C(1) methylene), 2.99 (2 H, t, J~7 Hz, C(3) methylene), 2.67 (2 H, quintet, J~7 Hz, C(2) methylene); 2.52 (3 H, s, 7-methyl); mass spectrum (EI mode) m/z 295 and 297 (P+, $^{79}$Br and $^{81}$Br), 249 and 251 (P+-NO$_2$) Anal. Calcd for $C_{11}H_{10}BrN_3O_2$: C, 44.60; H, 3.40; N, 14.18. Found: C, 44.83; H, 3.31; N, 14.07.

5-Amino-7-methyl-2,3-dihydro-1H-pyrrolo[1,2-a] benzimidazole (25). A suspension of 550 mg (1.85 mmol) of 24 in 100 mL of methanol containing 90 mg of 5% palladium on carbon was shaken under 50 psi H$_2$ for 8 hours. The reaction mixture was filtered through Celite and the filter cake washed with methanol. Acidification of filtrate with few drops of 1N NCl and evaporation in vacuo afforded the dihydrochloride salt of 25. Recrystallization was carried out from ethyl acetate/methanol: 350 mg (72%) yield; dec pt 320° C.; TLC (chloroform/methanol, [90:10]), $R_f=0.39$; IR(KBr pellet), 3369, 3316, 3206, 2918, 2886, 2871, 1652, 1569, 1495, 1386 cm$^{-1}$; $^1$H NMR (dimethyl sulfoxide-d$_6$) δ6.74 and 6.54 (2 H, 2×s, C(6) and C(8) aromatic protons), 4.25 (2 H, t, J~7 Hz, C(1) methylene), 3.30 (2 H, t, J~7 Hz, C(3) methylene), 2.74 (2 H, quintet, J~7 Hz, C(2) methylene), 2.33 (3 H, s, 7-methyl); mass spectrum (EI mode) m/z 187 (P+ for 25). Anal. Calcd for $C_{11}H_{13}N_2.2HCl.0.25 H_2O$: C, 49.91; H, 5.71; N, 15.87. Found: C, 50.21; H, 5.29; N, 15.82.

7-Methyl-2,3-dihydro-1H-pyrrolo[1,2-a] benzimidazole-5,8-dione (26). To a suspension of 218 mg (0.83 mmol) of 25 in 10 mL of water, containing 200 mg of monobasic potassium phosphate, was added a solution of 1.34 g of Fremy's salt in 50 mL of water containing 500 mg of monobasic potassium phosphate. The reaction mixture was stirred at room temperature for 2 hours and extracted with 3×50 mL portions of chloroform. The dried extracts (sodium sulfate) were concentrated and then chromatographed over silica gel, employing chloroform as the eluant, to afford yellow-colored 26, 105 mg (61%) yield. Recrystallization from chloroform/hexane afforded analytically pure 26: mp 162°-164° C.; TLC (methanol chloroform[10:90]), $R_f=0.62$; IR(KBr pellet) 1675, 1659, 1647, 1515, 1154 cm$^{-1}$; $^1$H NMR (dimethyl sulfoxide-d$_6$) δ6.54 (1 H, quartet, J=1.6 Hz, C(6) proton coupled to 7-methyl), 4.16 (2 H, t, J~7 Hz, C(1) methylene), 2.86 (2 H, t, J~7 Hz, C(3) methylene), 2.62 (2 H, quintet, J~7 Hz, C(2) methylene), 2.00 (3 H, d, J=1.6 Hz, 7-methyl coupled to C(6) proton); mass spectrum (EI mode) m/z 202 (P+), 174 (P+-CO), 146 (P+-2CO), Anal. Calcd for $C_{11}H_{10}N_2O_2$: C, 65.33; H, 4.98; N, 13.85. Found: C, 65.15; H, 4.70; N, 13.61.

6-(Dimethylamino)-7-methyl-2,3-dihydro-1H-pyrrolo [1,2-a]benzimidazole-5,8-dione (27). To a solution of 50 mg (0.24 mmol) of 26 in 3 mL of dry DMF, chilled to 0° C., was added an excess of methanolic dimethylamine. After the addition, the reaction mixture was stirred at room temperature for about 30 min and then the solvent was evaporated in vacuo. The residue was chromatographed on silica gel employing chloroform as the eluant. The blue-colored 27 was obtained in 42 mg (71%) yield. An analytical sample was prepared by dissolving the residue in a small amount of chloroform, adding hexane, and then chilling the mixture overnight in the refrigerator: mp 158° C. dec; TLC (chloroform/methanol[90:10]), $R_f=0.56$, IR(KBr pellet) 1675, 1659, 1623, 1524, 1314, 1067 cm$^{-1}$; $^1$H NMR (CDCl$_3$) δ4.16 (2 H, t, J~7 Hz, C(1) methylene), 3.04 (6 H, s, dimethylamino), 2.87 (2 H, t, J~7 Hz, C(3) methylene), 2.64 (2 H, quintet, J~7 Hz, C(2) methylene); 1.93 (3 H, s, 7-methyl); mass spectrum (EI mode) m/z 245 (P+), 230 (P+-CH$_3$), 217 (P+-CO). Anal. Calcd for $C_{13}H_{15}N_3O_2.0.25$: C, 62.50; H, 6.15; N, 16.82. Found: C, 62.78; H, 6.32; N, 16.64.

6-(N-Aziridinyl)-7-methyl-2,3-dihydro-1H-pyrrolo [1,2-a]benzimidazole-5,8-dione (28). To a solution of 35 mg (0.17 mmol) of 26 in 4 mL of dry methanol, chilled at 0° C., was added 0.5 mL of ethyleneimine. The reaction was stirred at 0° for 30 min and then at room temperature for 1 hour. The solvent was removed in vacuo and the red residue flash chromatographed on silica gel using chloroform as the eluant. The purified product was recrystallized from chloroform/hexane: 20.5 mg (48%) yield; mp 192°-194° C. dec.; TLC (acetone), $R_f=0.73$; IR(KBr pellet) 1674, 1632, 1575, 1518, 1377, 1338, 1315, 1137, 988 cm$^{-1}$; $^1$H NMR (CDCl$_3$) δ4.17 (2 H, t, J~7 Hz, C(1) methylene), 2.89 (2H, t, J~7 Hz, C(3) methylene), 2.65 (2 H, quintet, J~7 Hz, C(2) methylene): 2.31 (4 H, s, aziridine protons), 2.02 (3 H, s, 7-methyl): mass spectrum (EI mode) m/z 243 (P+), 228 (P+-methyl). (Anal. Calcd for $C_{13}H_{13}N_3O_2$: C, 64.18; H, 5.34; N, 17.27. Found: C, 64.02; H, 5.21; N, 16.76.

6-Acetamido-7-methyl-5nitro-2,3-dihydro-1H-pyrrolo[1,2-a]benzimidazole-3-ol (29). To a suspension of 205 mg (0.61 mmol) of 15b in 10 mL of dry methanol was added 88 mg of $K_2CO_3$. The reaction was stirred at room temperature for 20 min and then concentrated in vacuo. The black residue was flash chromatographed on silica gel using a chloroform/methanol (98:2) mixture as the eluant. The yellow-colored product was recrystallized by dissolving it in a minimum amount of (4:1) chloroform/methanol, adding hexane, and then chilling: 141 mg (78%) yield: dec pt 259° C.; TLC (chloroform:methanol[20:80]) $R_f=0.35$, IR(KBr pellet) 3237, 3181, 3065, 1741, 1700, 1667, 1632, 1574, 1532, 1404 cm$^{-1}$; $^1$H NMR (dimethyl sulfoxide-d$_6$) δ9.67 (1 H, s, amide proton), 7.66 (1 H, s, C(8) proton), 5.97 (1 H, d, J=5.3 Hz, hydroxyl proton), 5.09 (1 H, m, C(3) proton), 4.22 and 4.05 (2 H, 2×m, C(1) diastereomeric methylene), 2.90 and 2.37 (2 H, 2×m, C(2) diastereomeric methylene), 2.27 (3 H, s, 7-methyl proton), 1.97 (3 H, s, acetamido methyl); mass spectrum (EI mode) m/z, 290(P+), 272(P+-H$_2$O), 248 (P+-ketene) 244 (P+-NO$_2$) Anal. Calcd for C$_{13}$H$_{14}$N$_4$O$_4$.0.75H$_2$O: C, 51.39; H, 5.13; N, 18.44. Found: C, 51.75; H, 4.77; N, 18.45.

6-Acetamido-7-methyl-5-nitro-2,3-dihydro-1H-pyrrolo[1,2-a]benzimidazole-3-Phenylcarbonate (30). To a solution of 200 mg (0.68 mmol) of 29 in 25 mL of dry pyridine, chilled at 0° C., was added 800 L of phenyl chloroformate. The reaction was stirred at 0° for 30 min and then at room temperature for 2 hours. The pyridine was evaporated in vacuo and the yellowish-red residue dissolved in 50 mL of chloroform. The chloroform solution was washed 2 times with dilute aqueous acetic acid (5%) and then 2 times with water. The extract was dried over Na$_2$SO$_4$ and then concentrated to a residue, which was dissolved in a chloroform/methanol (9:1) solution. Hexane was added to this solution until it became cloudy; chilling the solution in a refrigerator afforded pure 30: 194 mg (69%) yield; dec pt 245° C.; TLC (chloroform/methanol [80:20]) $R_f=0.44$; IR(KBr pellet) 1764, 1683, 1525, 1496, 1487, 1359, 1353, 1246, 1216, 1092 cm$^{-1}$; $^1$H NMR (dimethyl sulfoxide-d$_6$) δ9.79 (1 H, s, amide proton), 7.82 (1 H, s, C(8) proton), 7.47 and 7.32 (5 H, 2×m, phenyl), 6.23 (1 H, dd, J=7.7 Hz, J=3.2 Hz, C(3) proton), 4.39 and 4.27 (2 H, 2×m, C(1) diastereomeric methylene), 3.25 and 2.87 (2 H, 2×m, C(2) diastereomeric methylene), 2.36 (3 H, s, 7-methyl), 2.04 (3 H, s, acetamido methyl); mass spectrum (EI mode) m/z 410(P+), 392 (P+-H$_2$O), 364 (P+-PhOCO$_2$). Anal. Calcd for C$_{20}$H$_{18}$N$_4$O$_6$: C, 58.53; H, 4.42; N, 13.65. Found: C, 58.27; H, 4.37; N, 13.29.

6-Acetamido-7-methyl-5-nitro-2,3-dihydro-1H-pyrrolo[,1,2-a]benzimidazole-3-Carbamate ( 31). To a solution of 199 mg (0.48 mmol) of 30 in 150 mL of dichloromethane and methanol (9:1) was added 100 mL of liquid ammonia. The solution was kept at −76° C. for 30 min and then allowed to come to room temperature over a 3 hour period. The solvent was evaporated and the solid residue recrystallized from a mixture of chloroform-/methanol (90:10) and hexane: dec pt 266° C.; TLC (chloroform/methanol [80:20]) $R_f=0.3$; IR(KBr pellet) 3320, 3245, 1744, 1721, 1659, 1528, 1372, 1359, 1310, 1299, 1258, 1087 cm$^{-1}$; $^1$H NMR (dimethyl sulfoxide-d$_6$) δ9.74 (1 H, s, amide proton), 6.01 (1 H, dd, J=7.9 Hz, J=3.9 Hz, C(3) proton), 4.24 (2 H, m, C(1) diastereomeric methylene), 3.11 and 2.53 (2 H, 2×m, C(2) diastereomeric methylene), 2.37 (3 H, s, 7-methyl), 2.02 (3 H, s, acetamido methyl), mass spectrum (EI mode) m/z 333 (P+), 290 (P+-O=C=NH), 272 (P+-carbamic acid). Anal. Calcd for C$_{14}$H$_{15}$N$_5$O$_5$: C, 50.54; H, 4.23; N, 21.01. Found: C, 50.59; H, 4.56; N, 20.96.

6-Acetamido-7-methyl-5-amino-2,3-dihydro-1H-pyrrolo[1,2-a]benzimidazole-3-Carbamate (32). To a suspension of 130 mg (0.39 mmol) of 31 in 50 mL of methanol was shaken for 4 hours under 50 psi in the presence of 50 mg of 5% Pd on carbon. The catalyst was removed by filtration through Celite and the filtrate concentrated to dryness. The glassy residue was dissolved in 10 mL of a 90:10 chloroform/methanol mixture, to which hexane was added until cloudiness appeared. Chilling this mixture resulted in crystallization of white-colored 32: 107 mg (90%) yield; dec pt 229° C.; TLC (chloroform/methanol [80:20]), $R_f=0.27$; IR(KBr pellet) 3361, 3319, 3277, 1752, 1729, 1657, 1614, 1376, 1315, 1303 cm$^{-1}$; $^1$H NMR (dimethyl sulfoxide-d$_6$) δ8.89 (1 H, s, amide proton), 6.68 ( 2 H, br s, amide protons), 6.58 (1 H, s, C(8) proton), 5.95 (1 H, dd, J=7.4 Hz, J=3.2 Hz, C(3) proton), 4.92 (2 H, br s, amino), 4.07 (2 H, m, C(1) diastereomeric methylene), 3.o5 and 2.49 (2 H, 2×m, C(2) diastereomeric methylene), 2.15 (3 H, s, 7-methyl), 2.04 (3 H, s, acetamido methyl); mass spectrum (EI mode) m/z 303(P+), 260 (P+-H—N=C=O), 242 (P+-carbamic acid). Anal. Calcd for C$_{14}$H$_{17}$N$_5$O$_3$.0.25 H$_2$O: C, 54.62; H, 5.56; N, 22.75. Found: C, 54.71; H, 5.54; N, 22.62.

6-Acetamido-7-methyl-2,3-dihydro-1H-pyrrolo [1,2-a]benzimidazole-5,8-dione-3-Carbamate (33). To a suspension of 50 mg (0.16 mmol) of 32 in 5 mL water, containing 25 mg of monobasic potassium phosphate, was added a solution of 320 mg of Fremy's salt in 20 mL water containing 200 mg of monobasic potassium phosphate. The reaction mixture was stirred at room temperature for 2 hours and then extracted with 6×20 mL portions of chloroform. The combined extracts were dried over Na$_2$SO$_4$ and concentrated to a residue, which was recrystallized with chloroform/hexane: 28 mg (58%) yield; dec pt 205° C.; TLC (methanol/-chloroform [20:80]), $R_f=0.46$; IR(KBr pellet) 3467, 3410, 3377, 1789, 1753, 1694, 1675, 1611, 1520 cm$^{-1}$; $^1$H NMR (dimethyl sulfoxide-d$_6$)δ9.68 (1 H, s, amide proton), 6.79 (2 H, br s, amide proton), 5.92 (1 H, dd, J=7.6 Hz, J=3.2 Hz, C(3) proton), 4.27 (2 H, m, C(1) diastereomeric methylene), 3.08 and 2.52 (2 H, 2×m, C(2) diastereomeric methylene), 2.09 (3 H, s, 7-methyl), 1.83 (3 H, s, acetamido methyl); mass spectrum (EI mode) m/z 318 (P+), 276 (P+-ketene), 257 (P+-carbamic acid). Anal. Calcd for C$_{14}$H$_{14}$N$_4$O$_5$.0.5H$_2$O: C, 51.37; H, 4.31; N, 17.12. Found: C, 51.48; H, 4.27; N, 16.55.

6-Acetamido-5-imino-7-methyl-1H-pyrrolo[1,2-a]benzimidazol-8-one-3-Carbamate (34). To a suspension of 50 mg (0.16 mmol) 32 in 5 mL of 0.2 M pH 7.0 phosphate buffer (μ=1.0 KCl) was added the following: 130 mg of Fremy's salt solution in 10 mL of this buffer and then 5 mL of water. This mixture was stirred at room temperature for 40 min and the resulting red-colored solution extracted with 6×20 mL portions of chloroform. The combined extracts were dried over Na$_2$SO$_4$ and concentrated to a residue, which was recrystallized from chloroform/hexane: 19 mg (37%) yield; dec pt 259° C.; TLC (chloroform/methanol [80:20]), $R_f=0.35$; IR(KBr pellet) 3419, 3365, 1722, 1652, 1624, 1603, 1496, 1385, 1323, 1086 cm$^{-1}$; $^1$H NMR (dimethyl sulfoxide-d$_6$) δ9.33 (1 H, s, amide proton), 6.63 (3 H, m, amide and imine protons), 5.86 (1 H, m, C(3) proton), 4.39 (2 H, m, C(1) diastereomeric methylene), 3.19 and 2.48 (2 H, 2×m, C(2) diastereomeric methylene), 1.75 and 1.60 (6 H, 2×s, 7-methyl and acetamido methyl); mass spectrum (EI mode) m/z 317 (P+), 275 (P+-O=C=N—H), 256 (P+-carbamic acid). Anal. Calcd for C$_{14}$H$_{15}$N$_5$O$_4$.0.25H$_2$O: C, 52.24; H, 4.77; N, 21.76. Found: C, 52.40; H, 5.07; N, 19.16.

6-(Dimethylamino)-7-methyl-2,3-dihydro-1H-pyrrolo [1,2-a]benzimidazole-5,8-dione-3-Acetate (35). To a solution of 36 mg (0.13 mmol) of 9c in 2 mL of dry DMF, chilled at 0° C., was added 500 μL of methanolic dimethylamine. The reaction mixture was stirred at 0°

C. for 15 min and the solvent then evaporated in vacuo. The resulting blue solid was flash chromatographed on silica gel using chloroform as eluant. The purified product was recrystallized from chloroform/hexane: 28 mg (71%) yield; mp 74° C.; TLC (chloroform/methanol [90:10]) $R_f=0.67$; IR(KBr pellet) 1676, 1615, 1597, 1587, 1522, 1480, 1469, 1448, 1442, 1315 cm$^{-1}$; $^1$H NMR (CDCl$_3$) δ5.98 (1 H, dd, J=7.6 Hz, J=3.0 Hz, C(3) proton), 4.23 (2 H, m, C(1) diastereomeric methylene), 3.09 and 2.64 (2 H, 2×m, C(2) diastereomeric methylene), 3.03 (6 H, s, dimethylamino), 2.02 (3 H, s, 7-methyl), 1.91 (3 H, s, acetate methyl); mass spectrum (EI mode) m/z 303(P$^+$), 243(P$^+$-acetic acid).

6-(Dimethylamino)-7-methyl-2,3-dihydro-1H-pyrrolo [1,2-a]benzimidazole-5,8-dione-3-Carbamate (36). To a solution of 52 mg (0.19 mmol) of 9d in 2 mL of dry DMF, chilled at 0° C., was added 500 μL of dimethylamine solution in methanol (0.22 g/mL). The reaction mixture was stirred at 0° for 10 min and then at room temperature for 30 min. The solvent was evaporated in vacuo and the residue flash chromatographed on silica gel employing a (98:2) mixture of chloroform/methanol as the eluant: 55 mg (95%) yield; mp 123°-125° C.; TLC (acetone) $R_f=0.57$; IR(KBr pellet) 3463, 3401, 1725, 1680, 1622, 1618, 1525, 1383, 1317, 1089 cm$^{-1}$. $^1$H NMR (CDCl$_3$) δ5.98 (1 H, dd, J=7 Hz, J=3.2 HZ, C(3) proton), 4.76 (2 H, br s, amide proton), 4.31 (2 H, m, C(1) diastereomeric methylene), 3.11 (6 H, s, dimethylamino), 3.12 and 2.7 (2 H, 2×m, C(2) diastereomeric methylene), 2.01 (3 H, s, 7-methyl); mass spectrum (EI mode) m/Z 304 (p$^+$), 261 (p$^+$-O=C=N—H), 243 (P$^+$-carbamic acid). Anal. Calcd for C$_{14}$H$_{16}$N$_4$O$_4$. 0.25H$_2$O: C, 54.45; H, 5.22; N, 18.14. Found: C, 54.65; H, 5.02; N, 17.02.

Pyrrolo[1,2-a]benzimidazole (azamitosene) reductive alkylating agents synthesized as described above provide analogues 1c,d which are found to be potent antitumor agents in cloned human ovarian and colon cancer cell lines, as well as in fresh human ovarian and colon tumors.

The synthesis of iminoquinone derivatives (iminoazamitosenes) 2a,b is also described. Internal hydrogen bonding involving the 6-acetamido and the 4-nitrogen of the pyrrolo[1,2-a]benzimidazole ring serve to stabilize the imine group so that hydrolysis below pH 6 is extremely slow (see FIG. 1). Internal hydrogen bonding also influences the thermodynamics of buffer-catalyzed imine syn/anti isomerization. Thus, the foregoing synthetic and physical studies confirm that a variety of hydrolytically-stable iminoquinone reductive alkylating agents can be prepared. These iminoquinones will hydrolyse only under acidic conditions and hydrolytic stability is expected in a variety of cellular environments.

Our electrochemical studies indicate iminoquinone reductive alkylating agents will possess low oxygen toxicity. Iminoquinone 2a possesses much higher reduction potentials than its quinone analogue 1a. The reduced form of 2a (19) thus reoxidizes two orders of magnitude slower than the reduced form of 1a (20) in aerobic buffer at physiological pH. In contrast iminodaunomycin has low oxygen toxicity as a result of reductive deamination to afford a high reduction potential species unable to generate oxygen radicals efficiently.

From the foregoing, it is readily apparent that new and useful azamitosenes and iminoazamitosenes have been herein described and illustrated which fulfill all of the aforesaid objectives in a remarkably unexpected fashion. It is, of course, understood that such modifications, alterations and adaptations as will occur to the skilled artisan when confronted with this disclosure are intended within the spirit of the present invention which is limited solely by the scope of the claims appended hereto.

Accordingly, what is claimed is:

1. Azamitosenes having the structural formula:

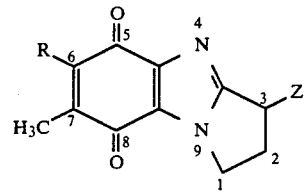

wherein:

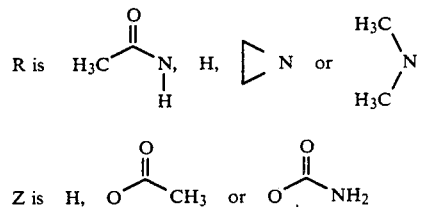

2. An azamitosene according to claim 1 in which R is hydrogen.

3. An azamitosene according to claim 1 in which R is azirdinyl.

4. An azamitosene according to claim 1 in which R is acetamido.

5. An azamitosene according to claim 1 in which R is dimethylamino.

6. An azamitosene according to claim 1 in which Z is hydrogen.

7. An azamitosene according to claim 1 in which Z is acetate.

8. An azamitosene according to claim 1 in which Z is carbamate.

9. An azamitosene according to claim 2 in which Z is hydrogen.

10. An azamitosene according to claim 2 in which Z is acetate.

11. An azamitosene according to claim 2 in which Z is carbamate.

12. An azamitosene according to claim 3 in which Z is hydrogen.

13. An azamitosene according to claim 3 in which Z is acetate.

14. An azamitosene according to claim 3 in which Z is carbamate.

15. An azamitosene according to claim 4 in which Z is hydrogen.

16. An azamitosene according to claim 4 in which Z is acetate.

17. An azamitosene according to claim 4 in which Z is carbamate.

18. An azamitosene according to claim 5 in which Z is hydrogen.

19. An azamitosene according to claim 5 in which Z is acetate.

20. An azamitosene according to claim 5 in which Z is carbamate.

21. Iminoazamitosenes having the structural formula:
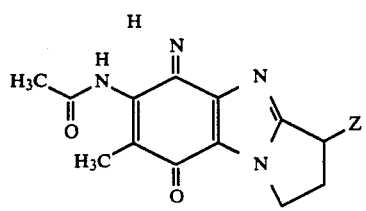
wherein:
Z is H, 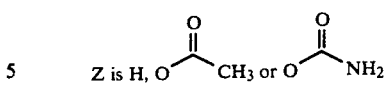
22. An iminoazamitosene according to claim 21 in which Z is hydrogen.
23. An iminoazamitosene according to claim 21 in which Z is acetate.
24. An iminoazamitosene according to claim 21 in which Z is carbamate.
* * * * *

UNITED STATES PATENT AND TRADEMARK OFFICE
CERTIFICATE OF CORRECTION

PATENT NO. : 5,015,742

DATED : May 14, 1991

INVENTOR(S) : Edward B. Skibo, et al.

It is certified that error appears in the above-identified patent and that said Letters Patent is hereby corrected as shown below:

The title page should be deleted, to appear as per attached title page.

Signed and Sealed this

Twelfth Day of May, 1992

Attest:

DOUGLAS B. COMER

*Attesting Officer*   *Acting Commissioner of Patents and Trademarks*

United States Patent [19]

Skibo et al.

[11] Patent Number: 5,015,742

[45] Date of Patent: May 14, 1991

[54] SYNTHESIS AND ELUCIDATION OF AZAMITOSENE AND IMINOAZAMITOSENE

[75] Inventors: Edward B. Skibo, Scottsdale; Imadul Islam, Tempe, both of Arizona

[73] Assignee: Arizona Board of Regents, Tempe, Ariz.

[21] Appl. No.: 486,977

[22] Filed: Feb. 28, 1990

[51] Int. Cl.$^5$ .................. C07D 235/30; C07D 235/04; C07D 487/00

[52] U.S. Cl. .................................... 548/323; 548/325; 548/327

[58] Field of Search ...................... 548/325, 323, 327

Primary Examiner—Mary C. Lee
Assistant Examiner—Joseph K. McKane
Attorney, Agent, or Firm—Richard R. Mybeck

[57] ABSTRACT

The synthesis of 2,3-dihydro-1H-pyrrolo[1,2-a]benzimidazole-5,8-diones (azamitosenes was carried out in conjunction with the design of potential DNA cross-linkers activated by reduction (reductive alkylation). These quinones resemble mitosene antitumor agents, but are based on the benzimidazole nucleus rather than the indole nucleus. Preliminary results indicate the azamitosenes are potent antitumor agents. Iminoquinone derivatives of azamitosenes (iminoazamitosenes) were synthesized as reductive alkylating agents exhibiting low oxygen toxicity. The iminoazamitosenes are hydrolytically stable in neutral buffers and undergo buffer catalyzed syn/anti isomerization at the imino center. Electrochemical and oxygen reactivity studies in aqueous buffers indicate the change from quinone to iminoquinone is accompanied by an increase in reduction potential and a decrease in oxygen reactivity of the corresponding reduced species.

24 Claims, 1 Drawing Sheet